(12) United States Patent
Tapia Espriu et al.

(10) Patent No.: US 11,690,622 B2
(45) Date of Patent: Jul. 4, 2023

(54) ADJUSTABLE PRESSURE SURGICAL CLAMP WITH RELEASABLE OR INTEGRATED REMOTE MANIPULATOR FOR LAPAROSCOPIES

(71) Applicants: Roberto Tapia Espriu, San Antonio, TX (US); Javier Carrillo Silva, Morelia (MX)

(72) Inventors: Roberto Tapia Espriu, San Antonio, TX (US); Javier Carrillo Silva, Morelia (MX)

( * ) Notice: Subject to any disclaimer, the term of this patent is extended or adjusted under 35 U.S.C. 154(b) by 233 days.

(21) Appl. No.: 17/155,235

(22) Filed: Jan. 22, 2021

(65) Prior Publication Data

US 2021/0212688 A1    Jul. 15, 2021

Related U.S. Application Data

(62) Division of application No. 15/624,323, filed on Jun. 15, 2017, now Pat. No. 10,898,192.

(51) Int. Cl.
| | |
|---|---|
| *A61B 17/10* | (2006.01) |
| *A61B 17/08* | (2006.01) |
| *A61B 17/00* | (2006.01) |
| *A61B 17/28* | (2006.01) |
| *A61B 17/29* | (2006.01) |

(52) U.S. Cl.
CPC ........ *A61B 17/10* (2013.01); *A61B 17/00234* (2013.01); *A61B 17/08* (2013.01); *A61B 17/282* (2013.01); *A61B 17/29* (2013.01); *A61B 2017/294* (2013.01); *A61B 2017/2924* (2013.01); *A61B 2017/2931* (2013.01)

(58) Field of Classification Search
CPC ... A61B 17/10; A61B 17/00234; A61B 17/08; A61B 17/282; A61B 17/29; A61B 2017/2924; A61B 2017/2931; A61B 2017/294
See application file for complete search history.

(56) References Cited

U.S. PATENT DOCUMENTS

| | | | | |
|---|---|---|---|---|
| 987,173 | A | * 3/1911 | Salé | B25B 9/00 294/100 |
| 2,137,710 | A | * 11/1938 | Alfredw | A61B 17/2909 606/206 |

(Continued)

*Primary Examiner* — Phong Son H Dang
(74) *Attorney, Agent, or Firm* — Kammer Browning PLLC

(57) ABSTRACT

A surgical clamp for laparoscopic or endoscopic surgeries provides autonomous adjustable pressure and placement with a releasable or integrated remote manipulator. Two jaws move simultaneously with respect to the main body of the clamp to open and close to secure or release tissue and/or organs. In a first embodiment, the instrument is made up of two separable components; a remote manipulator component, and a releasable adjustable pressure clamp component that is linked or separated at an interlocking connection point. The main body of the clamp includes a central tubular port through which a pressure bar passes. An assembly of cam arms connects the push rod to jaws, allowing for symmetrical and simultaneous actuation. A compression spring is positioned around the pressure bar and is secured by an adjustable nut on the threaded end of the pressure bar. Adjustment varies the compressive force of the spring and thereby the gripping force.

3 Claims, 15 Drawing Sheets

(56) References Cited

U.S. PATENT DOCUMENTS

| | | | | |
|---|---|---|---|---|
| 2,212,013 | A * | 8/1940 | Devareaux | A47J 43/283 294/99.2 |
| 4,575,143 | A * | 3/1986 | Nast | B25J 1/04 294/24 |
| 4,830,002 | A * | 5/1989 | Semm | A61B 17/2909 294/100 |
| 4,987,634 | A * | 1/1991 | Weihrauch | A47L 13/022 15/210.1 |
| 5,052,402 | A * | 10/1991 | Bencini | A61B 10/06 600/564 |
| 5,258,005 | A * | 11/1993 | Christian | A61B 17/29 606/205 |
| 5,304,183 | A * | 4/1994 | Gourlay | A61B 17/1285 606/41 |
| 5,449,361 | A * | 9/1995 | Preissman | A61B 17/8861 606/279 |
| 5,499,997 | A * | 3/1996 | Sharpe | A61B 17/221 606/205 |
| 5,628,757 | A * | 5/1997 | Hasson | A61B 17/062 606/205 |
| 5,695,504 | A * | 12/1997 | Gifford, III | A61B 17/12109 606/139 |
| 5,826,928 | A * | 10/1998 | Shang | B25B 11/002 294/100 |
| 5,893,875 | A * | 4/1999 | O'Connor | A61B 17/29 606/174 |
| 5,947,996 | A * | 9/1999 | Logeman | A61B 17/29 606/174 |
| 6,210,418 | B1 * | 4/2001 | Storz | A61B 17/1285 606/205 |
| 6,315,340 | B1 * | 11/2001 | Chen | E01H 1/12 294/100 |
| 6,425,910 | B1 * | 7/2002 | Hugueny | A61B 10/06 606/206 |
| 6,428,555 | B1 * | 8/2002 | Koster, Jr. | A61B 17/32053 604/184 |
| 6,527,793 | B1 * | 3/2003 | Valtchev | A61B 17/06 606/139 |
| 7,137,988 | B2 * | 11/2006 | Frye | A61B 17/062 606/147 |
| 7,691,126 | B2 * | 4/2010 | Bacher | A61B 17/29 606/1 |
| 8,104,806 | B1 * | 1/2012 | Shih | B25J 1/02 294/120 |
| 8,491,627 | B2 * | 7/2013 | Opolski | A61B 34/71 606/205 |
| 8,764,769 | B1 * | 7/2014 | Rodriguez-Navarro | A61B 17/2812 600/114 |
| 9,161,772 | B2 * | 10/2015 | Hyodo | A61B 17/29 |
| 9,181,666 | B2 * | 11/2015 | Shnol | E01H 1/12 |
| 10,058,343 | B2 * | 8/2018 | Malkowski | A61B 17/29 |
| 10,570,596 | B1 * | 2/2020 | Schneck | E03C 1/26 |
| 2003/0114839 | A1 * | 6/2003 | Looper | A61B 17/320016 606/1 |
| 2005/0131396 | A1 * | 6/2005 | Stanczak | A61B 17/320016 606/1 |
| 2005/0154411 | A1 * | 7/2005 | Breznock | A61B 17/320016 606/184 |
| 2005/0277959 | A1 * | 12/2005 | Cosgrove | A61B 17/1285 606/151 |
| 2006/0184161 | A1 * | 8/2006 | Maahs | A61B 18/1492 606/41 |
| 2008/0287926 | A1 * | 11/2008 | Abou El Kheir | A61B 17/3421 606/1 |
| 2008/0315605 | A1 * | 12/2008 | Shih | B25J 1/02 56/332 |
| 2012/0259325 | A1 * | 10/2012 | Houser | A61B 17/29 606/41 |
| 2013/0085341 | A1 * | 4/2013 | Nobis | A61B 17/29 600/213 |
| 2014/0088637 | A1 * | 3/2014 | Parihar | A61B 17/29 606/205 |
| 2014/0088638 | A1 * | 3/2014 | Parihar | A61B 17/29 606/1 |
| 2015/0012016 | A1 * | 1/2015 | Stone | A61B 17/0485 606/144 |
| 2015/0157317 | A1 * | 6/2015 | Bagaoisan | A61B 17/0469 606/148 |
| 2016/0312452 | A1 * | 10/2016 | Perry | E03C 1/302 |
| 2017/0150961 | A1 * | 6/2017 | Marczyk | A61B 17/0625 |
| 2017/0196635 | A1 * | 7/2017 | Brennan | A61B 17/29 |
| 2018/0271550 | A1 * | 9/2018 | Rodriguez-Navarro | A61B 17/1285 |

\* cited by examiner

ADJUSTABLE PRESSURE SURGICAL CLAMP WITH RELEASABLE OR INTEGRATED REMOTE MANIPULATOR FOR LAPAROSCOPIES

CROSS REFERENCE TO RELATED APPLICATIONS

This application claims the benefit under Title 35 United States Code § 121, as a Divisional of co-pending U.S. patent application Ser. No. 15/624,323, filed Jun. 15, 2017, the full disclosure of which is incorporated herein by reference.

BACKGROUND OF THE INVENTION

1. Field of the Invention

The present invention relates generally to surgical instruments and manipulable tools used in surgery. The present invention relates more specifically to releasable surgical clamps for use with laparoscopic and endoscopic surgeries. The present invention further relates to adjustable pressure clamps with remote manipulators for laparoscopic and endoscopic surgeries.

2. Description of the Related Art

Laparoscopic and endoscopic procedures typically require the surgeon to hold, pull, and move different organs and/or tissue during the surgical procedures. It is necessary for the surgeon to be able to reposition instruments that are used easily, accurately, and as often as may be required depending upon the different tissues and varying conditions encountered during the laparoscopic or endoscopic surgical procedure. It is important that any gripping or clamping tools used in such surgeries have the ability to vary the clamping force required by the surgeon in order to prevent the release of the tissue from the grip and at the same time prevent any unnecessary trauma to the tissue. If the tissue or organs release from the clamping devices during surgery, the result can be longer surgical and anesthesia times as well as traumatized or torn tissues if excessive force is used.

The nature of laparoscopic and endoscopic surgeries also demands that the internal area of the surgical site be as free as possible from a large number of surgical instruments. The instruments that must be situated within the surgical site should be readily visible and have ease of movement with organs or tissues being grasped in order to be removed or repositioned. It would therefore be beneficial to have a manipulator type clamping instrument that can exert adjustable autonomous pressure through a gripping force on tissue and/or organs in a surgical site, that could connect with other instruments or other clamping devices, and that would allow the surgeon to use the devices according to the needs of each operation, as the need for securing or moving an organ or tissue arises. It would be important for such versatile instruments to be small in configuration so as to not congest the abdominal cavity or other surgical site, or congest the operating table with unnecessary surgical assistants handling such instruments. It would be important that what surgical assistants are required be allowed freer, more comfortable and precise movement during the course of surgery so as to avoid as much as possible any additional trauma as is frequently caused by traditional laparoscopic forceps and the like.

SUMMARY OF THE INVENTION

The present invention therefore provides a surgical clamp with releasable grip for laparoscopic or endoscopic surgeries that provides autonomous adjustable pressure and easy placement with a remote manipulator. The surgical clamp component provides two jaws that move simultaneously with respect to the main body of the clamp to open and close to secure or release tissue and/or organs. The surgical instrument is made up of two primary, optionally separable components; a remote manipulator component, and a releasable or integrated adjustable pressure clamp component. A variety of different adjustable pressure clamps may be engaged with and released from the remote manipulator component. Distinct configurations for the adjustable pressure clamp component may include jaws appropriate for grasping plain tissue, fatty tissue, or tissue and organs with oval fluid-filled cross-sections, as well as mixed smooth and fatty tissue elements. At least one of the two jaws of the adjustable pressure clamp component includes an aperture through which a suture thread may be passed to connect with other instruments or other clamping devices that may be required by the surgeon. A second such suture aperture on the clamp body serves the same purpose. The two crossed jaws are joined together at a bolt (pivot point) that holds the jaws to the main body of the clamp. The main body of the clamp includes a center axis tubular port through which a push rod pressure bar passes. An assembly of cam arms connects the push rod to the jaws to allow for the symmetrical and simultaneous actuation of the jaws. The clamp may be placed on the tissue or organ with just enough force to prevent tears and still provide the desired pressure for a secure grip.

An opposite (proximal) end of the pressure bar includes a threaded end section on which a base centering aperture guides the pressure bar into the main body of the clamp. A compression spring is positioned around the pressure bar and is secured thereon and partially compressed by a nut positioned on the threaded end section of the pressure bar. Adjustment (rotation) of the nut varies the compression on the spring and thereby varies the gripping force between the jaws of the clamp.

DETAILED DESCRIPTION OF THE PREFERRED EMBODIMENTS

Figure 1:
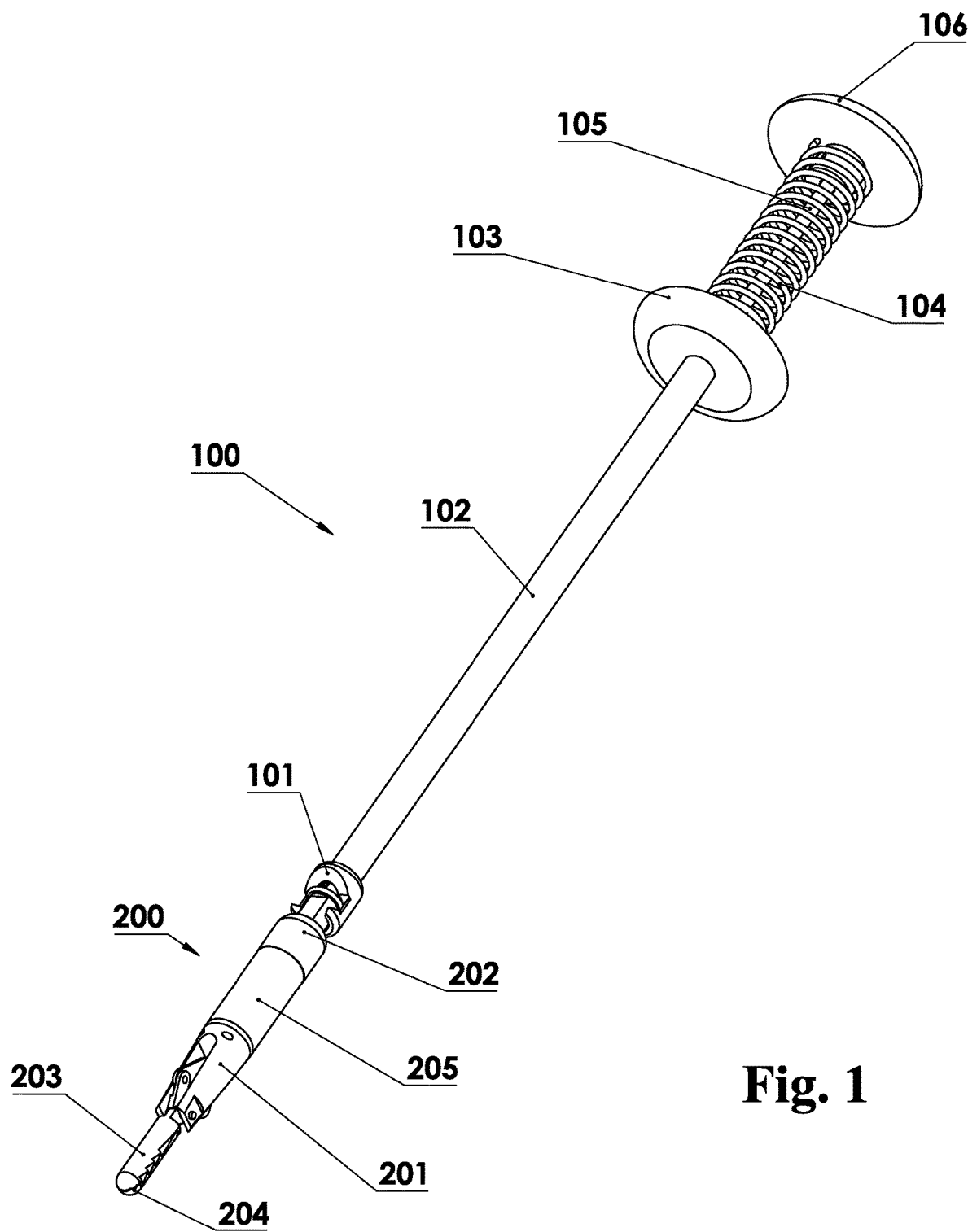
FIG. 1 is a perspective view of the surgical tool of the present invention shown in a jaw closed condition with the adjustable pressure clamp component connected to the remote manipulator component.

Reference is made first to FIG. 1 for a perspective view of the surgical tool of the present invention shown in a closed condition with the adjustable pressure clamp component connected to the remote manipulator component. Remote manipulator 100 is primarily a rigid tubular shaft constructed of outer casing 102 that terminates in external connector 101 at a distal end and in rear manipulator button 106 at a proximal end. Forward manipulator button 103 in this embodiment is fixed to outer casing 102. Internal to outer casing 102 and extending from the proximal end of the casing is manipulator shaft 105. In the view of FIG. 1, this proximal end of manipulator shaft 105 is shown surrounded by spring 104. Fixed to the proximal end of manipulator shaft 105 is rear manipulator button 106 which also serves to contain spring 104 between itself and forward manipulator button 103. With this structure, the user may compress spring 104 using forward and rear manipulator buttons 103 & 106 thereby directing manipulator shaft 105 into and through outer casing 102 of remote manipulator 100.

Connected to remote manipulator 100 in FIG. 1 is adjustable pressure clamp 200. The connection between these components is made between external connector 101 of remote manipulator 100 and internal connector 202 of adjustable pressure clamp 200. The manner of this connection and the operational interface at the connection are each described in more detail below.

Adjustable pressure clamp 200 is generally constructed of clamp body 201 which extends distally from clamp housing 205 which itself extends from internal connector 202 as shown. Clamp body 201 retains and supports a cam operated jaw assembly made up primarily of first jaw 203 and second jaw 204. The structure of the jaw components within clamp body 201 and their operative connections to remote manipulator 100 are described in more detail below.

Figure 2:
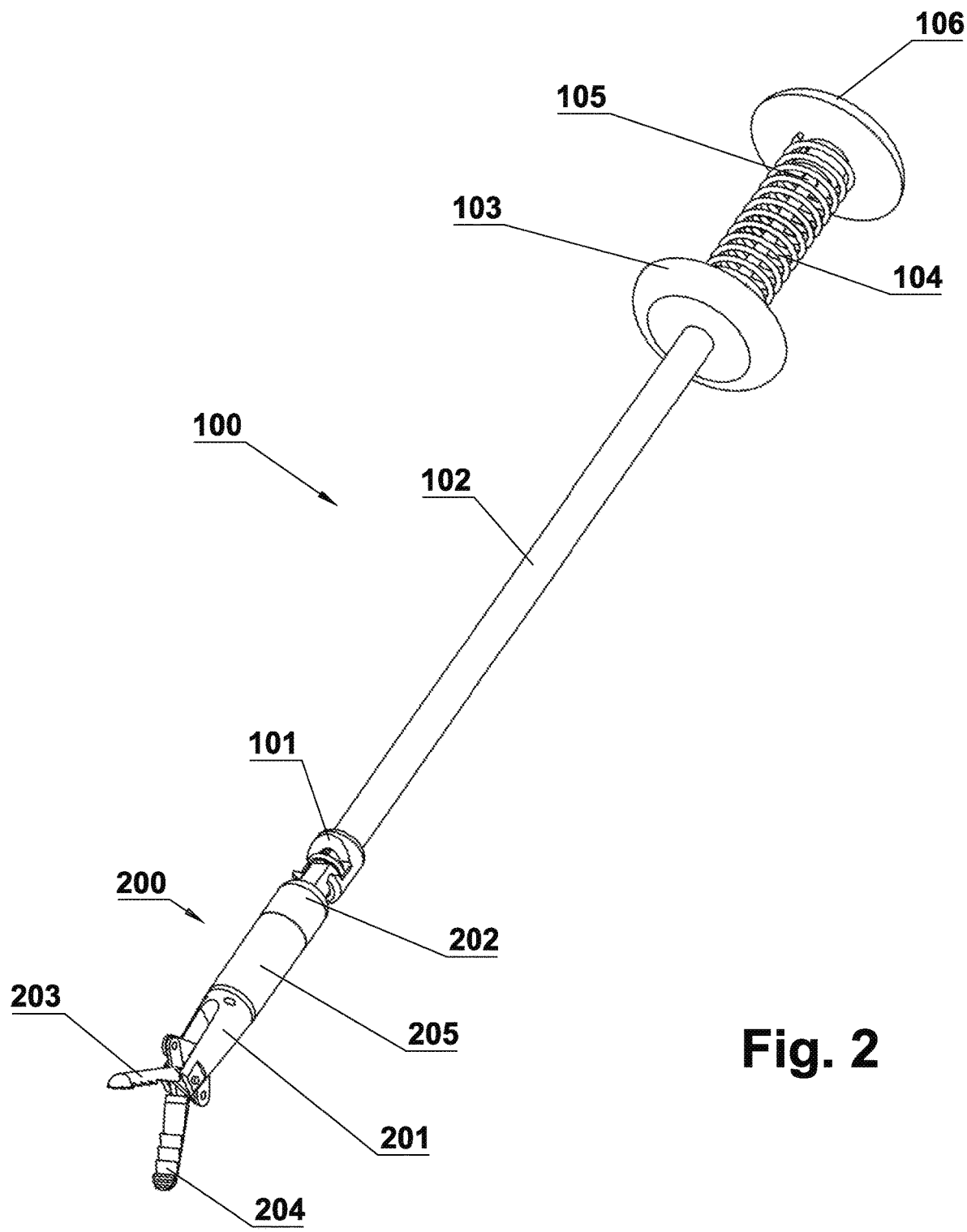
FIG. 2 is a perspective view of the surgical tool of the present invention shown in a jaw open condition, again with the adjustable pressure clamp component connected to the remote manipulator component.

Reference is next made to FIG. 2 which provides a view similar to that shown in FIG. 1 with remote manipulator 100 and adjustable pressure clamp 200 connected together at external connector 101 and internal connector 202. In the view of FIG. 2, however, the user has compressed spring 104 between forward manipulator button 103 and rear manipulator button 106, thereby directing manipulator shaft 105 through outer casing 102 of remote manipulator 100. This action directs the distal end of manipulator shaft 105 at or near the connection joint between remote manipulator 100 and adjustable pressure clamp 200, into the structure of internal connector 202 and clamp housing 205. Again, a cross-sectional view of this internal structure and its operation is described below. The result of directing manipulator shaft 105 through the connection as described above is to direct the opening of the adjustable pressure clamp 200 at clamp body 201 by the cam action of the clamp assembly and the spreading of first jaw 203 and second jaw 204 in a coordinated and coincident manner.

Figure 3:
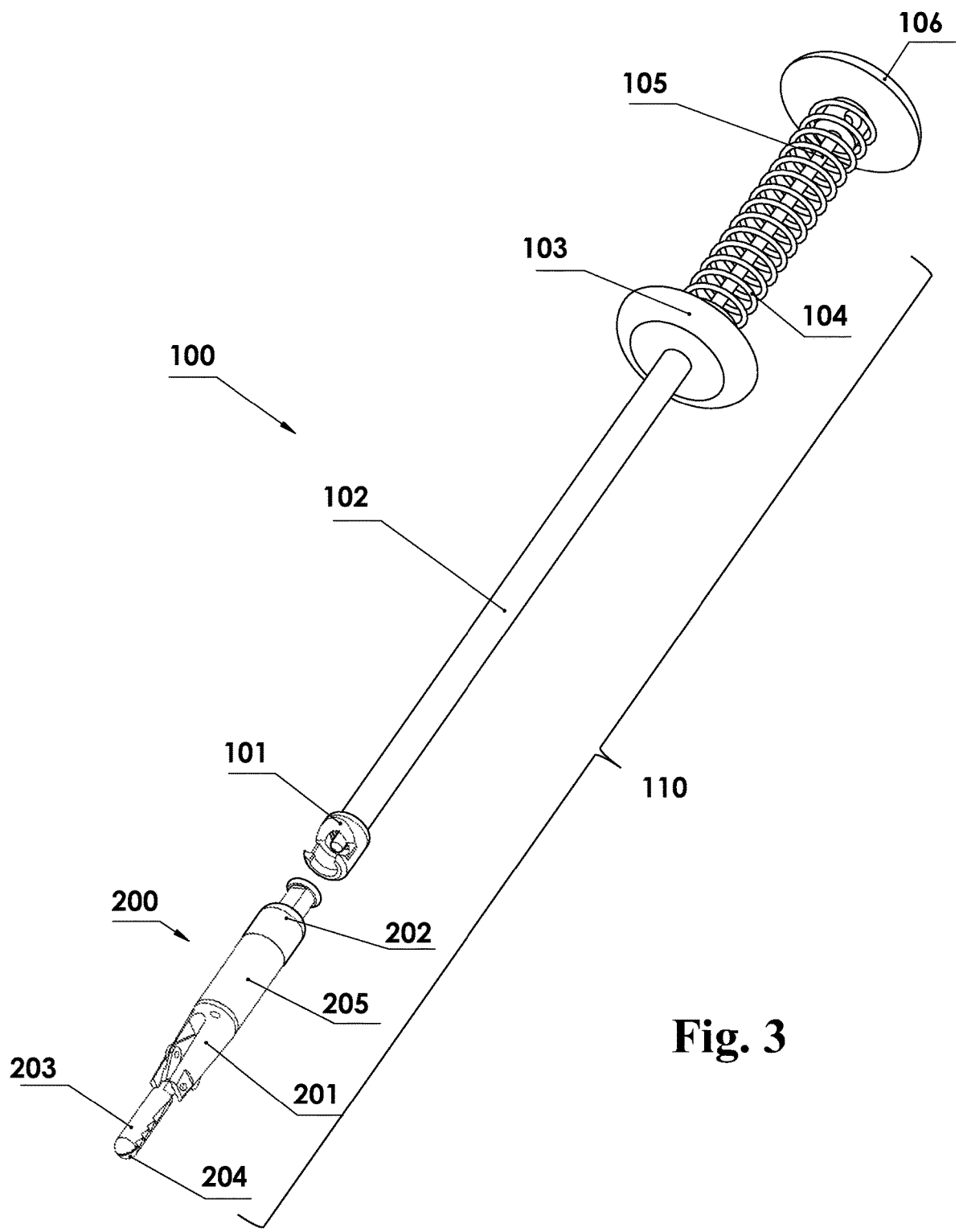
FIG. 3 is a perspective assembly view of the surgical tool of the present invention shown with the adjustable pressure clamp component in a jaw closed condition and disconnected from the remote manipulator component.

Reference is next made to FIG. 3 for a perspective assembly view of the surgical tool of the present invention shown in a jaw closed condition with the adjustable pressure clamp disconnected from the remote manipulator. Surgical tool 110 in FIG. 3 is again shown to be made up of its two primary components; remote manipulator 100 and adjustable pressure clamp 200. Once again, remote manipulator 100 is constructed primarily of a rigid tubular shaft with outer casing 102 surrounding an internal manipulator shaft 105. In the view of FIG. 3, spring 104 in the handle portion of remote manipulator 100 is extended and presses rear manipulator button 106 apart from forward manipulator button 103, thereby partially withdrawing manipulator shaft 105 from outer casing 102. External connector 101 as shown in FIG. 3 discloses in greater detail not only the manner of connection between remote manipulator 100 and adjustable pressure clamp 200 but also the concentric placement of manipulator shaft 105, with the distal end of the shaft just visible within external connector 101. If spring 104 were to be compressed by compressing forward manipulator button 103 and rear manipulator button 106 together, manipulator shaft 105 would extend out from external connector 101 to the same extent that remote manipulator 100 is compressed.

In FIG. 3, adjustable pressure clamp 200 is again seen generally as it is shown in FIG. 1. Internal connector 202 is shown separated from its saddle engagement with external connector 101. First jaw 203 and second jaw 204 are shown closed together under the influence of an internal spring (not shown) within clamp housing 205. Once again, the manner in which manipulator shaft 105 passes through the connection between the primary components and opens the adjustable pressure clamp (first jaw 203 and second jaw 204) is described in more detail below with respect to cross-sectional views of the adjustable pressure clamp 200.

Figure 4A:
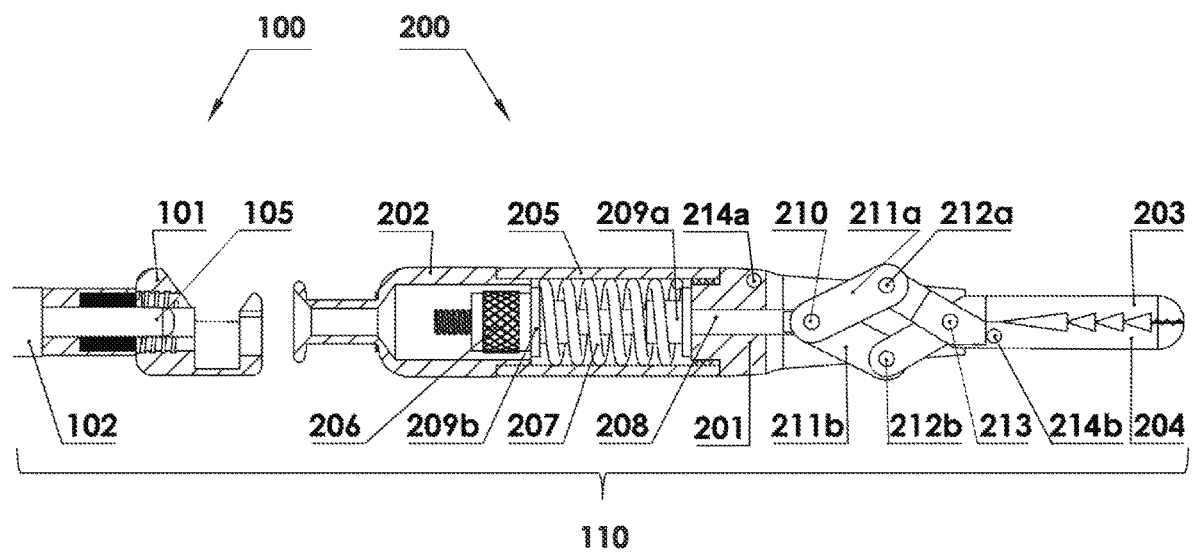
FIG. 4A is a detailed partial cross-sectional assembly view of the surgical tool of the present invention shown with the adjustable pressure clamp component in a jaw closed condition and disconnected from the remote manipulator component, with the manipulator shaft moved to an opposite end by the manipulator handle as shown in FIG. 4B, prepared to connect with the adjustable pressure clamp.
Figure 4B:
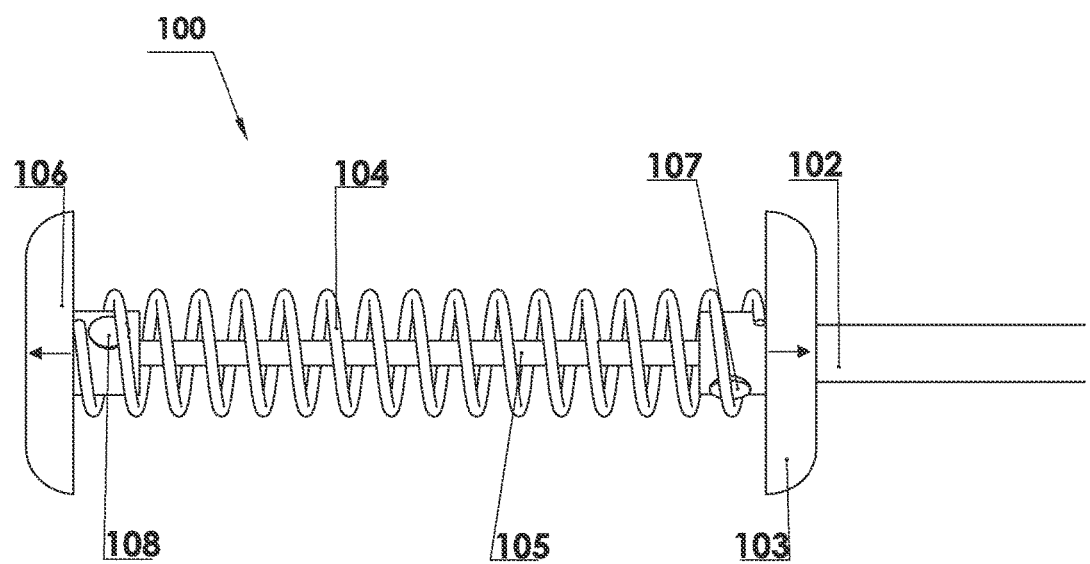
FIG. 4B is a detailed side view of the handle end of the remote manipulator component of the present invention shown with the spring extended between the separated buttons, prepared to connect with the adjustable pressure clamp component, which is in a jaw closed condition.

Reference is next made to FIGS. 4A & 4B for a detailed description of the internal structures operable to provide the functionality of the surgical tool of the present invention. FIG. 4A is a detailed partial cross-sectional assembly view of the surgical tool of the present invention shown with the adjustable pressure clamp component in a jaw closed condition disconnected from the remote manipulator component. FIG. 4A further provides a cross-sectional view of the connector end of the remote manipulator when manipulator shaft 105 is moved inside outer casing 102 by the action described below with regard to FIG. 4B. FIG. 4B is a detailed side view of the condition of the handle portion of the remote manipulator component when spring 104 is extended, pressing rear manipulator button 106 apart from forward manipulator button 103 and thereby withdrawing manipulator shaft 105 from outer casing 102 as shown in FIG. 4A.

FIG. 4A is a partial cross-sectional assembly view that shows the internal structure of the distal end of remote manipulator 100 and the internal structure of the proximal end of adjustable pressure clamp 200 at the connection point between these components. For clarity, these two components of surgical tool 110 are shown disconnected at external connector 101 and internal connector 202. The distal end of remote manipulator 100 shown in FIG. 4A includes the distal end of outer casing 102 which terminates with a threaded attachment to external connector 101. Manipulator shaft 105 is shown completely retracted into outer casing 102 as with the extension of the handle portion of remote manipulator 100 (see FIG. 4B below). The cross-sectional view of FIG. 4A shows the basic structure of the saddle or chamfer connection that is made between external connector 101 and internal connector 202. The manner in which adjustable clamp 200 can be positioned at an angle with respect to remote manipulator 100, whereby the fluted end of internal connector 202 is allowed to drop into and be partially secured and aligned by the chamfer of external connector 101 is described in more detail below.

FIG. 4A further discloses the internal structures and operable components of adjustable pressure clamp 200. Clamp body 201 is a solid cylindrical component threaded into clamp housing 205 at the proximal end of clamp body 201, and extending a pair of flat parallel plates in a yoke on either side of the cam operated jaw assembly on a distal end thereof. Clamp body 201 also incorporates suture aperture 214a for the purpose of allowing the surgeon to secure or retain adjustable pressure clamp 200 within the surgical site (either to tissue or to other devices) using suture thread or the like. A similar suture aperture 214b is configured in second jaw 204 for the same purpose.

Extending in a movable pivoting assembly within clamp body 201 is the arrangement of cam arms 211a & 211b. These cam arms 211a & 211b pivot on, and are rotatably fixed to, cap screw 210 which secures them to the distal end of pressure bar 208. Pressure bar 208 is itself movably positioned within clamp body 201 within the yoke formed by clamp body 201. On the distal side of cam arms 211a & 211b are the lever arm structures for first jaw 203 and second jaw 204. The scissor like jaw structures are rotatably fixed in position on clamp body 201 at jaw bolt 213 which extends between the two yoke plates that surround the cam arm assembly. In the view of FIG. 4A, one of the two yoke plates is seen positioned behind and supporting the cam arm assembly, while the second is removed for clarity in this partial cross-sectional view.

Clamp housing 205 is an open cylindrical housing internally threaded at its distal end to engage the externally threaded proximal end of clamp body 201. Clamp housing 205 is easily removable from clamp body 201 by rotating clamp housing 205 to unthread the threaded joint between the two clamp components. When clamp housing 205 is removed from clamp body 201, the internal operable structures of adjustable pressure clamp 201 are exposed to allow for adjustment of the clamping force.

Pressure bar 208 extends through the center of clamp body 201 and is capable of longitudinal movement therein. Again, cap screw 210 secures cam arms 211*a* & 211*b* to the distal end of pressure bar 208. Internal spring 207 is positioned around pressure bar 208 with a distal end of spring 207 positioned against the proximal face of clamp body 201, preferably separated and centered by way of centering washer 209*a*. The proximal end of internal spring 207 is held by a second centering washer 209*b* and is secured in place by way of adjustable nut 206 which is threaded onto the threaded proximal end of pressure bar 208. Adjustable nut 206 is preferably a knurled knob with internal threading that the user may rotate to vary the pre-set compression in the internal spring 207 and thereby vary the pre-set force with which the first jaw 203 and second jaw 204 clamp together.

It is clear from the structures of the internal mechanism of adjustable pressure clamp 200 that the preferenced position of first jaw 203 and second jaw 204 is in the closed condition as directed by the expansion force of internal spring 207 against clamp body 201 and against adjustable nut 206, which force in turn pulls pressure bar 208 in a proximal direction thereby closing the clamp by way of the cam arm assembly described above. Sufficient threading is provided on the proximal end of pressure bar 208 to allow for significant variability within the rotational adjustment and lateral placement of adjustment nut 206, thereby providing a range of spring tension from very weak clamping force (with adjustment nut 206 near to the end of pressure bar 208) to a significant clamping force (with adjustment nut 206 fully compressing internal spring 207) rotated fully onto the threaded portion of pressure bar 208.

FIG. 4B shows the external condition of the handle end of remote manipulator 100 when it is disconnected from adjustable pressure clamp 200 as in the arrangement shown in FIG. 4A. In this view, outer casing 102 is shown where it is fixed to forward manipulator button 103 by way of set screw 107 through a collar portion of manipulator button 103. Once again, manipulator shaft 105 moves freely in a longitudinal direction in and out of outer casing 102. The proximal end of manipulator shaft 105 is fixed to rear manipulator button 106 by way of set screw 108 which secures a collar portion of the manipulator button to the proximal end of manipulator shaft 105. The arrows on rear manipulator button 106 and forward manipulator button 103 indicate the direction of the force exerted between buttons 103 & 106 by spring 104, withdrawing manipulator shaft 105 up to the point where it is completely inside the outer casing 102 in a condition to be connected or disconnected from adjustable pressure clamp 200.

Figure 5A:
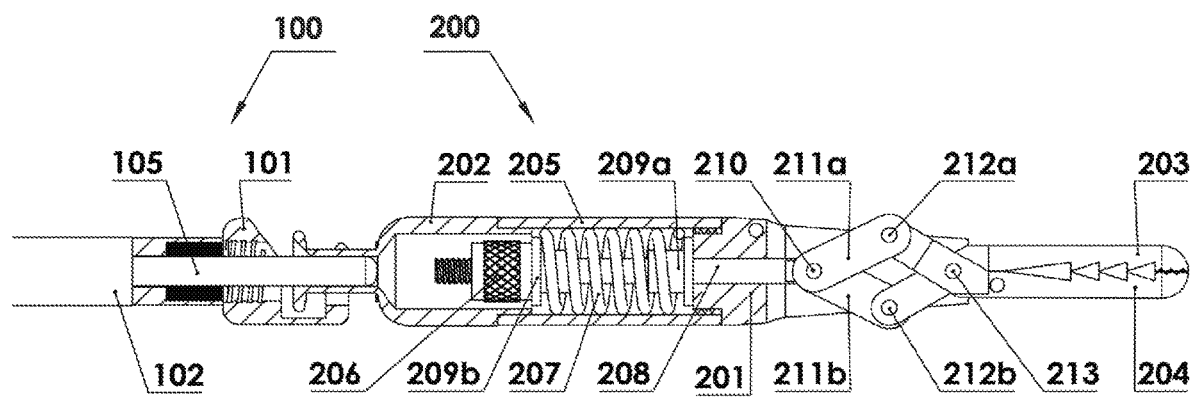
FIG. 5A is a detailed partial cross-sectional view of the surgical tool of the present invention shown with the adjustable pressure clamp component in a jaw closed condition and connected to the remote manipulator component.
Figure 5B:
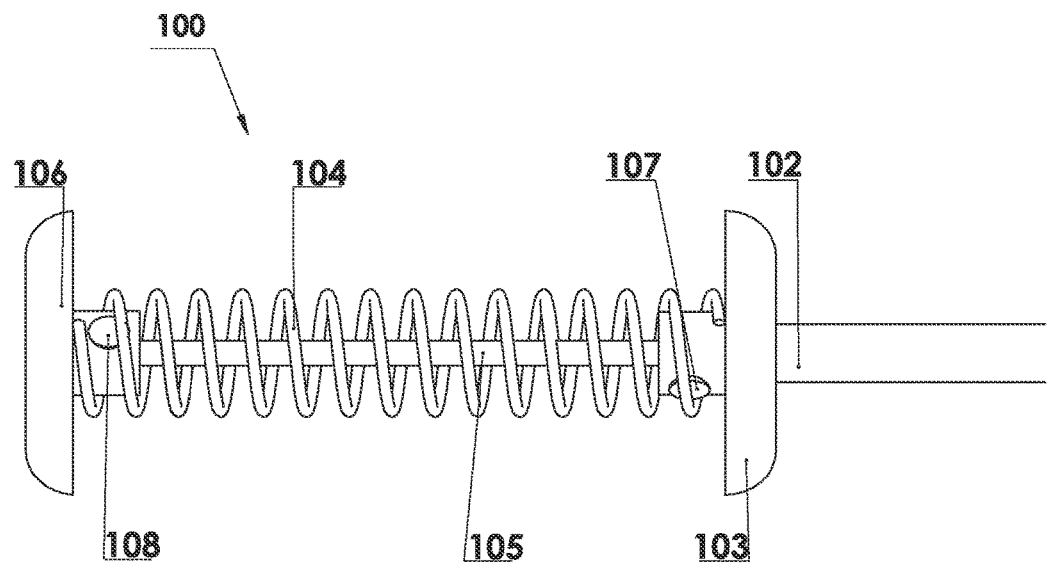
FIG. 5B is a detailed side view of the handle end of the remote manipulator component of the present invention shown as it would appear with the handle spring and manipulator buttons in a relaxed (uncompressed) condition with the adjustable pressure clamp component in a jaw closed position when connected with the adjustable pressure clamp component as in FIG. 5A.

Reference is next made to FIGS. 5A & 5B for a detailed description of the structure of the surgical tool configured with remote manipulator 100 and adjustable pressure clamp 200 connected together for use. In FIG. 5A a portion of outer casing 102 of remote manipulator 100 is shown terminating with its threaded attachment to external connector 101, where it engages and connects with internal connector 202 of adjustable pressure clamp 200. In addition to the two primary components being connected together, manipulator shaft 105 has been moved longitudinally into the fluted collar of internal connector 202, with spring 104 in a relaxed condition and with manipulator buttons 103 & 106 (see FIG. 5B) not exerting any force on spring 104. As a result, remote manipulator 100 and adjustable pressure clamp 200 are coupled and locked together and the condition of adjustable pressure clamp 200 in FIG. 5A remains essentially the same as that described above with FIG. 4A. Internal spring 207 continues to preference jaws 203 & 204 of the device closed by pressing back on adjustable nut 206 which engages the threaded portion of pressure bar 208 and draws the pressure bar back to pull on cam arms 211*a* & 211*b* to maintain jaws 203 & 204 in a closed configuration.

As indicated above, the manually operated end of remote manipulator 100 is in a relaxed condition as shown in FIG. 5B as a result of the user releasing any compressive force between rear manipulator button 106 and forward manipulator button 103. With manipulator shaft 105 fixed by way of set screw 108 to rear manipulator button 106, any change in this release action will begin to direct manipulator shaft 105 into outer casing 102 of remote manipulator 100. In the view shown in FIG. 5B, this action has been only just initiated, and as a result only a small portion of the distal end of manipulator shaft 105 has been directed into the connected adjustable pressure clamp 200 (see FIG. 5A) thereafter locking the coupling between the components.

Figure 6A:
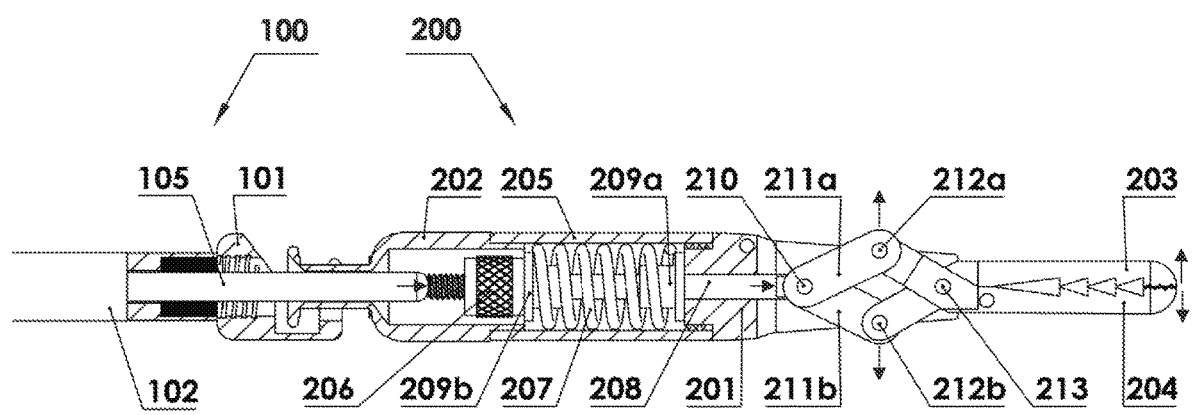
FIG. 6A is a detailed partial cross-sectional view of the surgical tool of the present invention shown with the adjustable pressure clamp component in a jaw closed but about to open condition when connected to the remote manipulator component and with the manipulator shaft engaging the pressure bar of the clamp component.
Figure 6B:
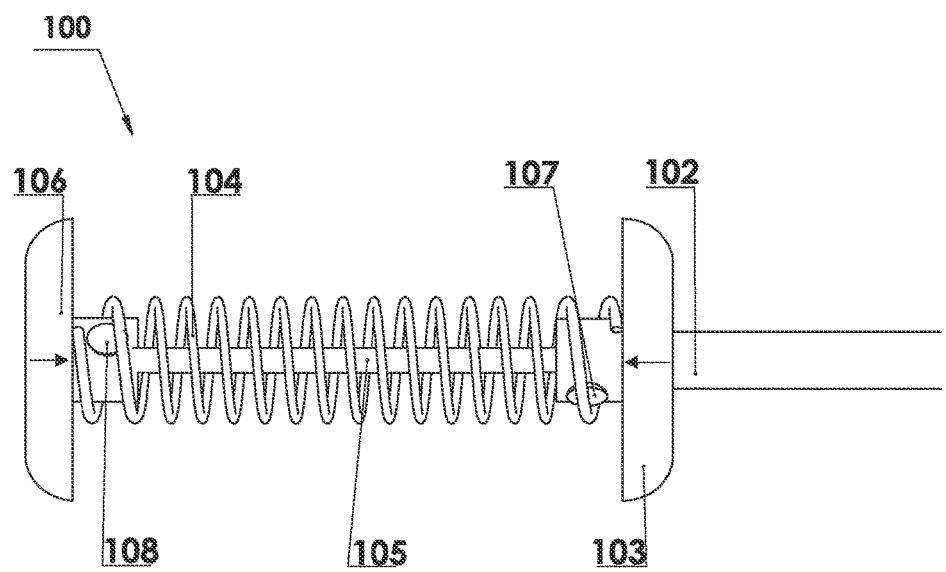
FIG. 6B is a detailed side view of the handle end of the remote manipulator component of the present invention shown applying compression to the spring by closing the distance between the manipulator buttons, thus engaging the manipulator shaft against the pressure bar of the adjustable pressure clamp component, the clamp in a jaw closed but about to open condition as in FIG. 6A.

Reference is next made to FIGS. 6A & 6B which show the further progression of the operation of the surgical tool of the present invention as a result of the initial compression of the proximal end (handle portion) of remote manipulator 100. In FIG. 6B, rear manipulator button 106 and forward manipulator button 103 have been compressed together counteracting the expansive force of spring 104 and directing manipulator shaft 105 further into outer casing 102. The directional arrows shown in FIG. 6B on manipulator buttons 106 & 103 indicate the direction of the compressive force being exerted by the user.

This compression of the proximal end (handle portion) of remote manipulator 100 results in the extension of manipulator shaft 105 further into adjustable pressure clamp 200 as shown in FIG. 6A. The distal end of manipulator shaft 105 is now in contact with the proximal end of pressure bar 208 at its threaded portion immediately behind adjustable nut 206 all within clamp housing 205. This contact between the two longitudinal components, and the ongoing longitudinal movement of manipulator shaft 105 directs a force along pressure bar 208 against the expansive preferencing force of internal spring 207 to direct pressure bar 208 distally forward to operate the cam arm assembly that terminates in first jaw 203 and second jaw 204. With pressure bar 208 rotatably fixed to the proximal ends of cam arms 211*a* & 211*b*, the cam arms move outward as shown by the arrows in FIG. 6A, thereby rotating first jaw 203 and second jaw 204 on pivot point jaw bolt 213 in a scissor like motion. This begins to release the clamping forces that have maintained first jaw 203 and second jaw 204 together and begins to direct the jaws outward (see arrows at the tips of the jaws in FIG. 6A) and open as a result.

Figure 7A:
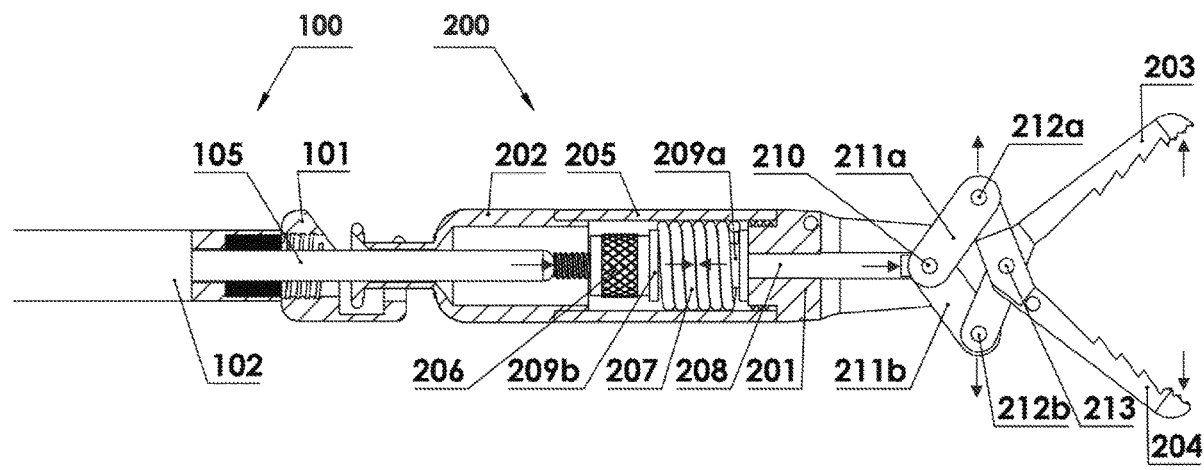
FIG. 7A is a detailed partial cross-sectional view of the surgical tool of the present invention shown with the adjustable pressure clamp component in a jaw open condition and connected to the remote manipulator component.
Figure 7B:
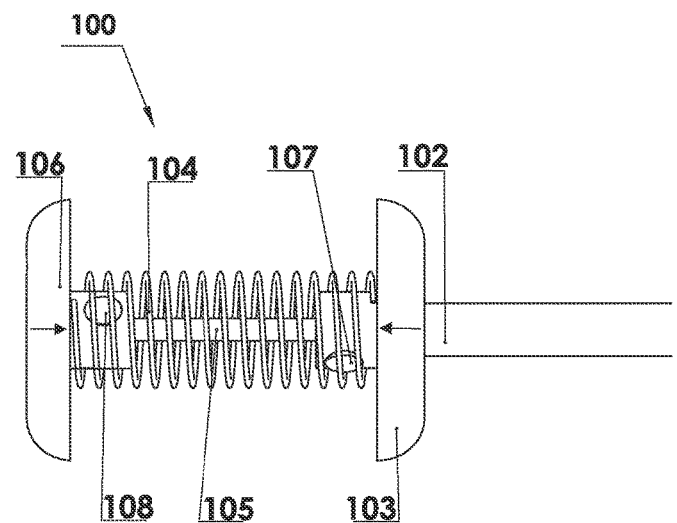
FIG. 7B is a detailed side view of the handle end of the remote manipulator component of the present invention shown as it would appear when the handle spring is compressed and with the adjustable pressure clamp component in a jaw open condition as in FIG. 7A.

Reference is next made to FIGS. 7A & 7B for a detailed description of the condition of the surgical tool when the handle portion of the remote manipulator 100 has been fully compressed by the user so as to effect the full opening of the jaws of adjustable pressure clamp 200. As seen in FIG. 7B, rear manipulator button 106 has been further compressed, as indicated by the directional arrows, against the expansive force of spring 104 positioned between manipulator buttons 106 & 103. This compression directs manipulator shaft 105 further into outer casing 102 where it remains as long as the user continues to exert compressive force to overcome the expansive force of spring 104. Through operation of the handle portion of remote manipulator 100, the surgeon may readily adjust the position and placement of adjustable pressure clamp 200 within the surgical site. Releasing the compression of the manipulator buttons 106 & 103 results in the pressure clamp closing with the degree of force that has been pre-set by the adjustment mechanism within the adjustable pressure clamp component of the surgical tool. With the setting shown in FIG. 7A for the adjustable nut 206 within adjustable pressure clamp 200, internal spring 207 reaches its full compression, thereby stopping the longitudinal distal movement of pressure bar 208 and manipulator shaft 105. The user will therefore encounter a stop at this point of compression even though spring 104 within the handle portion of remote manipulator 100 (see FIG. 7B) might not be fully compressed.

As shown in FIG. 7A, manipulator shaft 105 has extended fully into adjustable pressure clamp 200 within clamp housing 205 longitudinally into contact with the proximal end of pressure bar 208 as indicated. This fully compresses internal spring 207 (as shown by the compression arrows on the spring) and directs pressure bar 208 forward (distally) to its full extent, thereby moving cam arms 211a & 211b forward and out. Through the connection of cam arms 211a & 211b to first jaw 203 and second jaw 204 at cam bolts 212a & 212b, the motion pivots the jaws on jaw bolt 213 so as to rotate the jaws outward. This releases any engaged organ or tissue that may have been previously associated with the use of adjustable pressure clamp 200, or prepares adjustable pressure clamp 200 to engage.

The above description, representing the structures disclosed in FIGS. 4A & 4B through FIGS. 7A & 7B demonstrates the manner in which adjustable pressure clamp 200 may be fitted onto remote manipulator 100, inserted into the surgical site with the jaws of the clamp closed, and then opened within the surgical site to begin the process of engaging tissue and/or organ elements within the surgical site. It should be recognized that the release of a compressive force on the manipulator buttons 106 & 103 at the handle or proximal end of remote manipulator 100 will allow the jaws of the adjustable pressure clamp 200 to again close with the clamping force that has been pre-set through the prior adjustment of adjustable nut 206 within clamp housing 205. The surgeon may, for example, pre-set the clamping force on any of a number of different adjustable clamps 200 for various specific uses within the surgical site during the laparoscopic or endoscopic surgery. Some vessels, for example, may require a very light clamping force, while others may require greater clamping force. It will also be recognized that the structure of the jaws of the clamp may vary according to the intended use of the specific adjustable pressure clamp. The object of the releasable connection between the remote manipulator 100 and each adjustable pressure clamp 200 is to allow the surgeon to position and place multiple adjustable pressure clamps within the surgical site and then release them once they have been positioned appropriately. The surgeon may then remove the remote manipulator 100, fix it to a further adjustable pressure clamp 200 and begin the process of inserting the new clamp and using it within the surgical site. In this manner, it is unnecessary to position multiple manipulators through an endoscopic or laparoscopic incision thereby preventing the crowding of the surgical site with both clamps and manipulator handles.

Figure 8A:
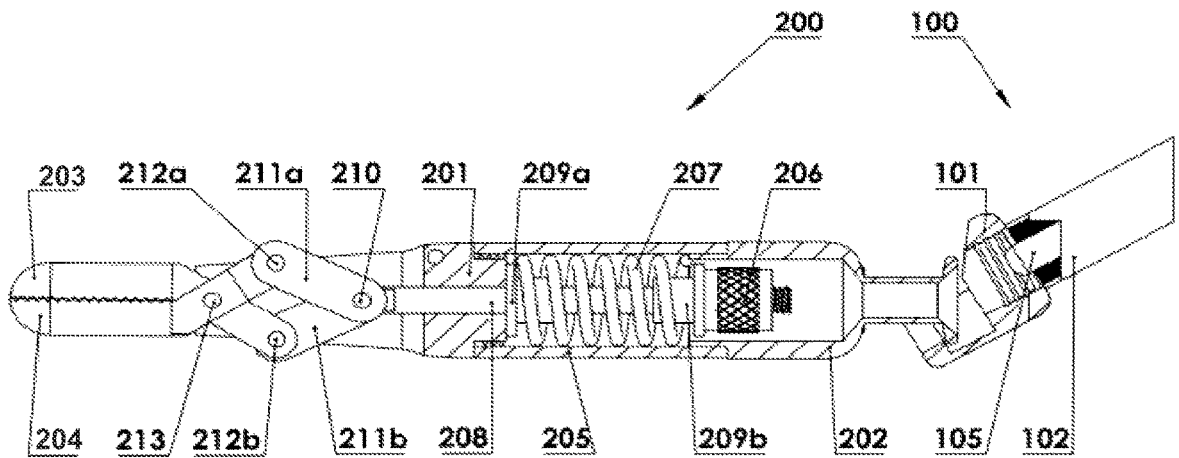
FIG. 8A is a detailed partial cross-sectional view of the surgical tool of the present invention shown with the adjustable pressure clamp component in a jaw closed condition as it is being attached at an angle to the remote manipulator component.
Figure 8B:
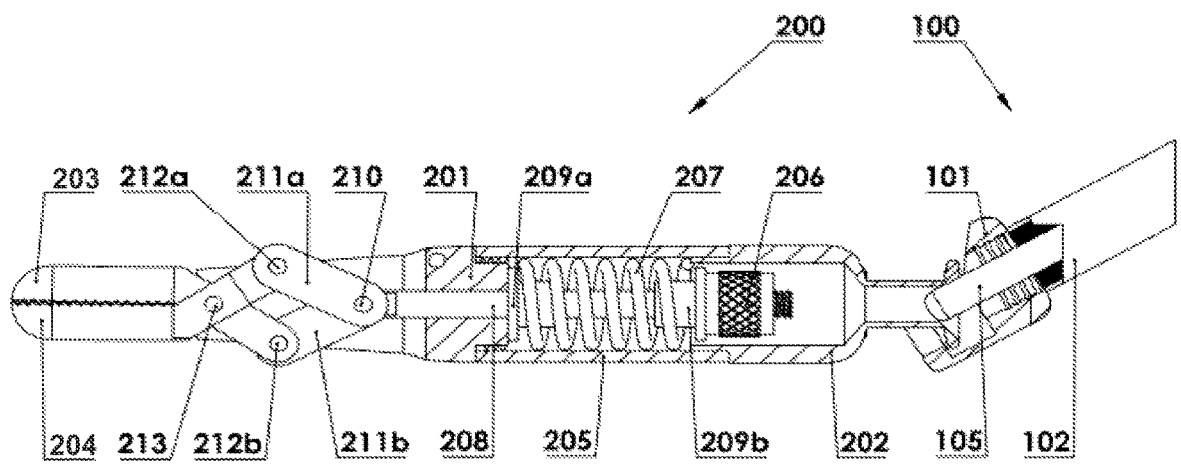
FIG. 8B is a detailed partial cross-sectional view of the surgical tool of the present invention shown with the adjustable pressure clamp component in a jaw closed condition as it is being attached at an angle to the remote manipulator component with alignment being assisted by extension of the manipulator shaft.
Figure 8C:
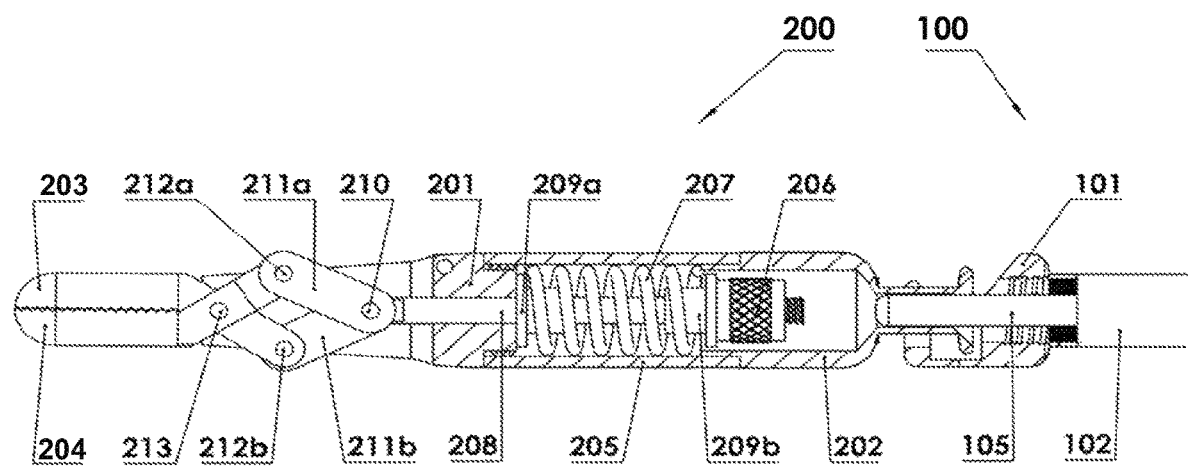
FIG. 8C is a detailed partial cross-sectional view of the surgical tool of the present invention shown with the adjustable pressure clamp component in a jaw closed condition as it is fully attached to the remote manipulator component, aligned and locked into alignment by extension of the manipulator shaft.

Reference is next made to FIGS. 8A-8D for a detailed description of the manner in which the adjustable pressure clamp component of the present invention may be connected to and released from the remote manipulator component. FIGS. 8A-8C show the progression of steps associated with the engagement and securement of remote manipulator 100 onto adjustable pressure clamp 200. The reverse process of releasing adjustable pressure clamp 200 from remote manipulator 100 is, of course, the reverse of the steps shown. The structure of adjustable pressure clamp 200 in the embodiment shown in FIGS. 8A-8D is essentially the same as that shown in FIG. 4A, albeit with a distinct, but still representative, jaw clamping surface structure.

FIG. 8A shows the manner in which remote manipulator 100 is initially positioned adjacent to adjustable pressure clamp 200 with the user allowing the expansive force of spring 104 to separate buttons 103 & 106 as in FIG. 4B explained above. By this action, manipulator shaft 105 is moved within manipulator outer casing 102 and begins the process of connecting with, adjustable pressure clamp 200. External connector 101 on remote manipulator 100 is structured to allow for engagement between the components when remote manipulator 100 is oriented at approximately a 30° angle from linear alignment with adjustable pressure clamp 200. This approximately 30° angle allows the fluted cylindrical end structure of internal connector 202 on adjustable pressure clamp 200 to be inserted from the side into the semi-circular chamfered edge saddle structure (see FIG. 8D) of external connector 101. The otherwise loose engagement between internal connector 202 and external connector 101 is made secure, once linearly aligned, by the passage of manipulator shaft 105 through each of the connector elements. At the same time, the user may release pressure between the buttons 103 & 106 thereby releasing the pressure on spring 104. The manner of securing the components together once linearly aligned is described in more detail below.

The balance of adjustable pressure clamp 200 shown in FIG. 8A is as described above with respect to FIG. 4A. The expansion force of internal spring 207 pushes outward against centering washers 209a & 209b which in turn exerts a force that draws back on pressure bar 208 centered within clamp body 201. Clamp housing 205 surrounds the adjustable force mechanism made up of pressure bar 208, internal spring 207, and adjustable nut 206. The jaw assembly shown in FIG. 8A is also as described above in FIG. 4A and is generally made up of first jaw 203 and second jaw 204 connected to cam arms 211a & 211b which operate in a pivoting arrangement off of the distal end of pressure bar 208 where they are secured with cap screw 210. First jaw 203 and second jaw 204 operate in a scissor like manner, pivoting on jaw bolt 213 which rotationally secures the jaws to the parallel yoke plate extensions of clamp body 201.

In practice, the user may carry out the steps associated with connecting adjustable pressure clamp 200 to remote manipulator 100 outside of the surgical site prior to insertion of the surgical tool, or may make this connection internal to the surgical site, as for example, after a specific adjustable pressure clamp 200 has already been positioned and placed within the surgical site to grip and hold tissue. In either case, the process of securing remote manipulator 100 to adjustable pressure clamp 200 further proceeds as shown in FIG. 8B. In this cross-sectional diagram, remote manipulator 100 is held at the same or an angle similar to that in the arrangement shown in FIG. 8A, that is at an angle to the linear axis of adjustable pressure clamp 200. The user now operates the handle portion of remote manipulator 100 so as to direct manipulator shaft 105 partially out from outer casing 102 through external connector 101. As manipulator shaft 105 extends from outer casing 102 and through external connector 101 it engages, again at an angle, the interior walls of the fluted cylindrical structure associated with the proximal end of internal connector 202. The interior walls of internal connector 202 on its fluted end have the same or similar degree of angle to match and accept manipulator shaft 105 when directed from the angle at which remote manipulator 100 is held. Extending partially into internal connector 202, manipulator shaft 105 helps the user direct manipulator shaft 105 further into adjustable pressure clamp 200 while beginning the process of moving the two components into alignment along the same linear axis. In other words, as shown in FIG. 8B, remote manipulator 100 may be simultaneously tilted downward (in the view of FIG. 8B) so as to align with adjustable pressure clamp 200, all the while manipulator shaft 105 continues to extend into and through the now engaged external connector 101 and internal connector 202.

FIG. 8C shows the completion of the process of connecting the adjustable pressure clamp component and the remote manipulator component of the present invention together for use, placement, or clamp removal. The fluted cylindrical portion of internal connector 202 now sits internally within external connector 101. Any linear movement of adjustable pressure clamp 200 away from remote manipulator 100 is restricted by the semi-circular, chamfered edge saddle portion of external connector 101. All other movement of internal connector 202 with respect to external connector 101 is limited by the stabilizing extension of manipulator shaft 105 through each part of the connection. Absent manipulator shaft 105, the two connector portions could, of course, be separated by sideways movement or by angled movement such as shown above in FIG. 8A. With manipulator shaft 105 present and even partially extended, however, the connection between the two primary components of the surgical instrument of the present invention is secure even when the user is not holding the surgical tool.

Figure 8D:
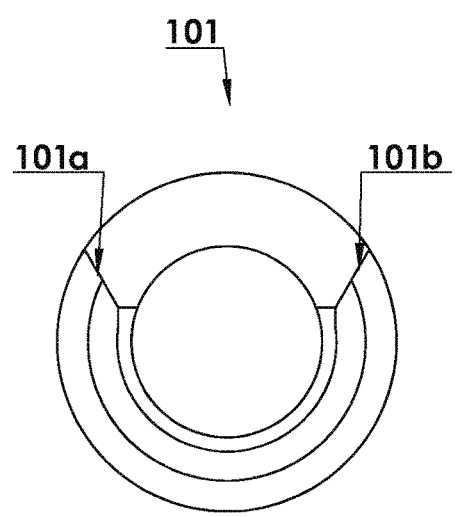
FIG. 8D is a detailed front (distal) view of the external connector of the remote manipulator component of the present invention showing the chamfer structure which guides alignment with the internal connector of the adjustable pressure clamp component.

Reference is next made to FIG. 8D, which provides a profile end view of external connector 101 fixed to the distal end of remote manipulator 100, looking back along the length of the remote manipulator 100. In this view, the saddle extension portion of external connector 101 is shown to incorporate a semi-circular rim with an opening (on top in the orientation of FIG. 8D) that extends from chamfer guide edge 101a to chamfer guide edge 101b. These chamfered edges allow the user to easily guide the fluted portion of internal connector 202 on adjustable pressure clamp 200 into alignment with the remote manipulator in a manner that allows the user to thereafter gradually releasing the pressure on buttons 103 & 106, maintain alignment between the components, and maintain a secure connection for the purpose of positioning and placing the specific adjustable pressure clamp component during surgery. Once positioned and placed, the user may reverse the process of securement by allowing the preferenced withdrawal of manipulator shaft 105 by allowing the separation of buttons 103 & 106 and the expansion of spring 104, which thereby allows for the angled removal of external connector 101 from internal connector 202 and therefore the removal of remote manipulator 100 from its connection to adjustable pressure clamp 200.

Figure 9A:
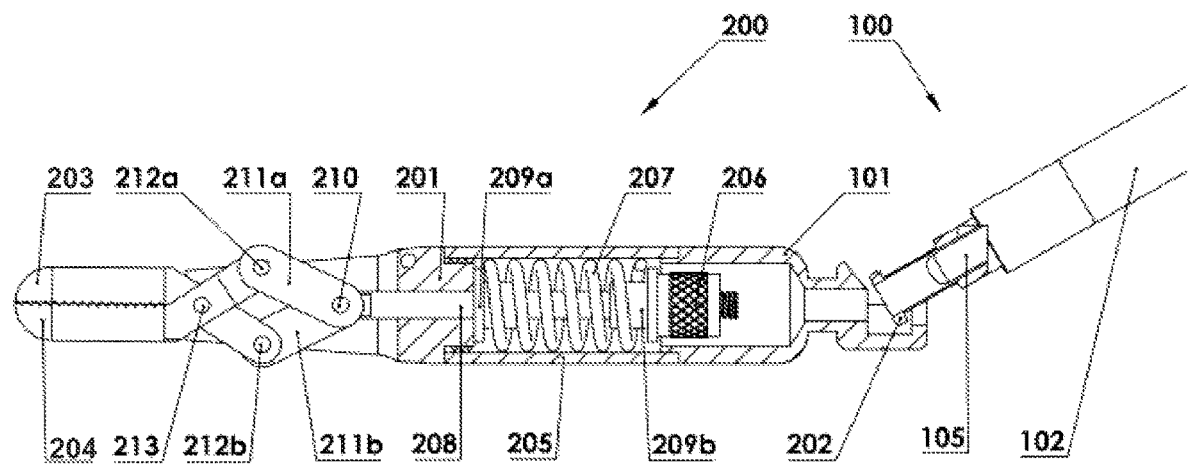
FIG. 9A is a detailed partial cross-sectional view of an alternate embodiment of the surgical tool of the present invention shown with the adjustable pressure clamp component in a jaw closed condition as it is being attached at an angle to the remote manipulator component.
Figure 9B:
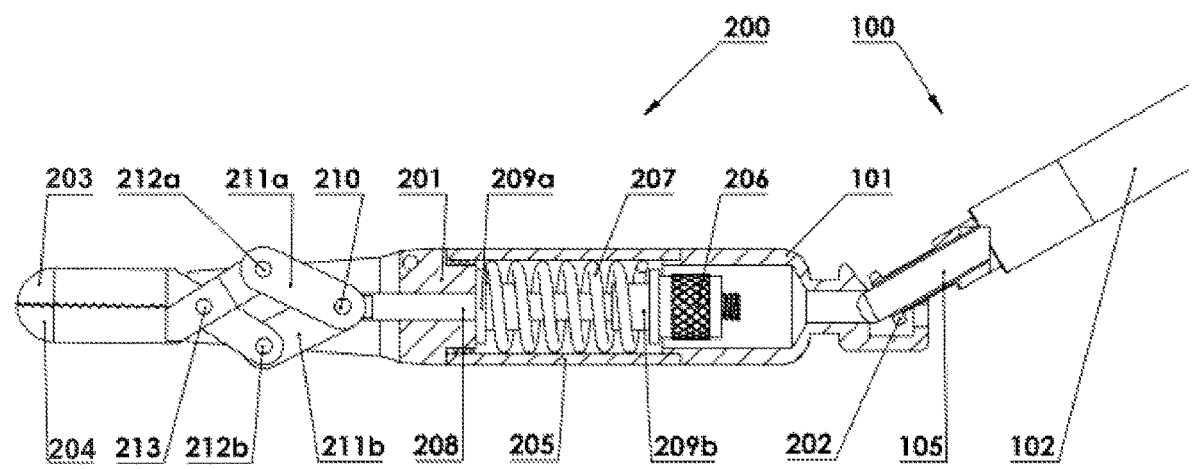
FIG. 9B is a detailed partial cross-sectional view of the alternate embodiment of the surgical tool of the present invention disclosed in FIG. 9AB, shown with the adjustable pressure clamp component in a jaw closed condition as it is being attached at an angle to the remote manipulator component with alignment being assisted by extension of the manipulator shaft.
Figure 9C:
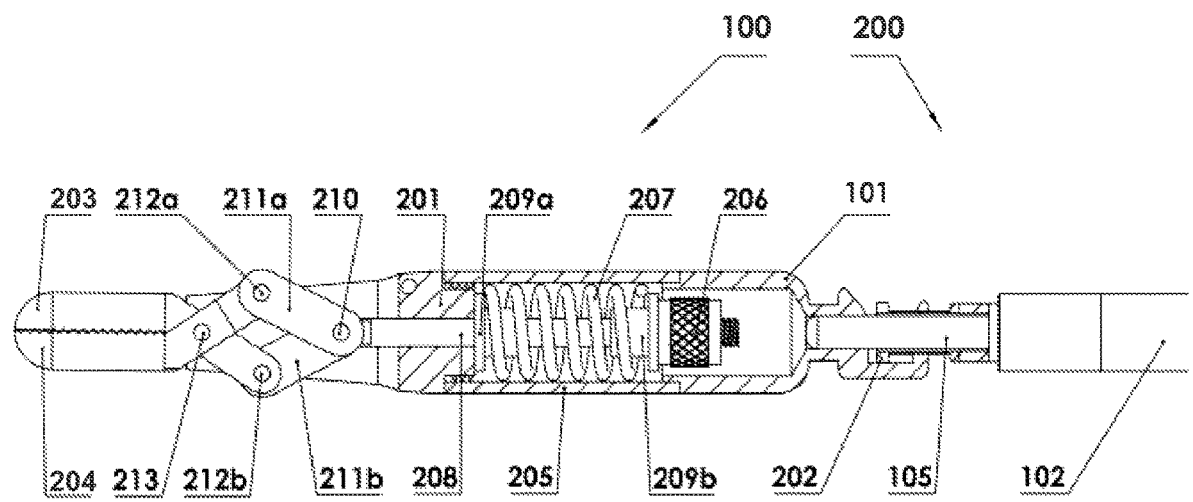
FIG. 9C is a detailed partial cross-sectional view of the alternate embodiment of the surgical tool of the present invention disclosed in FIG. 9A, shown with the adjustable pressure clamp component in a jaw closed condition as it is fully attached to the remote manipulator component, aligned and locked into alignment by extension of the manipulator shaft.

Reference is next made to FIGS. 9A-9D for a detailed description of an alternate structure for the connection interface elements on the adjustable pressure clamp component and the remote manipulator component of the present invention. The structural embodiments shown in FIGS. 9A-9D essentially switch external connector 101 from its placement on remote manipulator 100 to an opposing placement on adjustable pressure clamp 200. In turn, internal connector 202 is switched from its placement on adjustable pressure clamp 200 to an opposing position on remote manipulator 100. FIGS. 9A-9C therefore show the progression of steps associated with the engagement and securement of the alternate embodiment remote manipulator 100 on to the alternate embodiment adjustable pressure clamp 200. As before, the process of releasing adjustable pressure clamp 200 from remote manipulator 100 is the reverse of the steps shown progressively in FIGS. 9A-9C. The structure of adjustable pressure clamp 200 in the embodiment shown in FIGS. 9A-9D is essentially the same as that shown in FIGS. 8A-8D with the exception of the placement of external connector 101 on adjustable pressure clamp 200 and the placement of internal connector 202 on remote manipulator 100.

FIG. 9A shows the manner in which remote manipulator 100 is initially positioned adjacent to adjustable pressure clamp 200 where the user has allowed the expansive force of spring 104 to separate buttons 103 & 106 as in FIG. 4B referenced above, and by this action manipulator shaft 105 is withdrawn into manipulator outer casing 102 whereby the user may initiate the process of connecting with adjustable pressure clamp 200. In this case, external connector 101 on adjustable pressure clamp 200 is structured to allow for engagement between the components when remote manipulator 100 is again oriented at approximately a 30° angle from linear alignment with adjustable pressure clamp 200. This approximate 30° angle allows the flanged cylindrical structure of internal connector 202 on remote manipulator 100 to be dropped from the side or above into the semi-circular chamfer edged saddle structure (see FIG. 9D) of external connector 101 as positioned on adjustable pressure clamp 200. As before, the otherwise loose engagement between internal connector 202 and external connector 101 is made secure, once linearly aligned, by the passage of manipulator shaft 105 through each of the connector elements, and wherein the user may release the pressure between buttons 103 & 106 thereby releasing pressure on spring 104.

The balance of adjustable pressure clamp 200 is structured in essentially the same manner as shown in FIG. 4A. Only the connection between the two primary components of the surgical tool has been reversed. As with the original orientation of internal connector 202 and external connector 101, the user may carry out the steps associated with connecting adjustable pressure clamp 200 to remote manipulator 100 outside of the surgical site, or may make the connection internal to the surgical site. There are benefits to the connector structure associated with the embodiment shown in FIGS. 9A-9D, where the distal (operative) end of the remote manipulator component is less complex in structure. There are, however, some surgical environments where there are benefits to having the less complex connector structure on the adjustable pressure clamp component, as in FIGS. 8A-8D.

The process of securing remote manipulator 100 to adjustable pressure clamp 200 with this alternate structural embodiment, further proceeds as shown in FIG. 9B. In this cross-sectional view, the remote manipulator is held at the same angle in the arrangement shown in FIG. 9A with respect to the linear axis of adjustable pressure clamp 200. The user manipulates the tool by gradually exerting pressure between buttons 103 & 106 at the handle portion of remote manipulator 100 in order to direct manipulator shaft 105 out from outer casing 102 through internal connector 202. As manipulator shaft 105 extends from outer casing 102 and through internal connector 202 it engages, at an angle, the interior edge of the cylindrical aperture formed in the saddle portion of external connector 101. In this alternate embodiment shown in FIGS. 9A-9D, it may be preferable to dome the end surface of manipulator shaft 105 in order to facilitate its engagement with the generally abrupt edge of the cylindrical aperture formed by external connector 101. Once again, extending partially into external connector 101, manipulator shaft 105 helps the user engage the cylindrical opening of adjustable pressure clamp 200, while beginning the process of aligning the two components along their linear axes. As shown in FIG. 9B, remote manipulator 100 may be simultaneously angled downward so as to align with adjustable pressure clamp 200, while manipulator shaft 105 continues to extend into and through the now engaged external connector 101 and internal connector 202 by gradually releasing the pressure between buttons 103 & 106.

FIG. 9C shows the completion of the process of connecting the adjustable pressure clamp component and the remote manipulator component of this alternate embodiment of the present invention. The adjustable pressure clamp component may now be moved into position, activated, and secured to the tissue within the surgical site as needed. The process for separating the adjustable pressure clamp component from the remote manipulator component proceeds with the reverse of the steps shown in FIGS. 9A-9C. With the connection made as shown in FIG. 9C, any linear movement of adjustable pressure clamp 200 away from remote manipulator 100 is restricted by the semi-circular, chamfer edged, saddle portion of external connector 101. All other movement of internal connector 202 with respect to external connector 101 is limited by the stabilizing extension of manipulator shaft 105 through each part of the connection. As before, without manipulator shaft 105 extended, the two connector portions could be separated by sideways or angled orientation and movement such as shown above in FIG. 9A. With manipulator shaft 105 present and extended, however, the connection between the two primary components of the surgical instrument of this alternate embodiment of the present invention is secure even when the user is not holding the surgical tool.

Figure 9D:
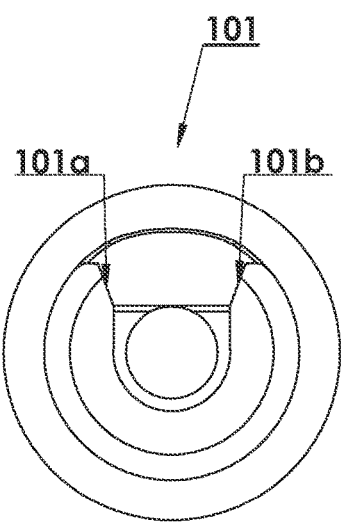
FIG. 9D is a detailed rear (proximal) view of the external connector, here positioned on the adjustable pressure clamp component in the alternate embodiment of the present invention, showing the chamfer structure which guides alignment with the internal connector, here positioned on the remote manipulator component in the alternate embodiment of the present invention.

Reference is next made to FIG. 9D which provides a profile view of external connector 101 fixed in this embodiment to the proximal end of adjustable pressure clamp 200 looking forward along the length of the adjustable pressure clamp. In this view, the saddle extension portion of external connector 101 is shown to incorporate a similar, albeit tighter, semi-circular rim with an opening (on the top in the orientation of FIG. 9D) that extends from chamfer guide edge 101*a* to chamfer guide edge 101*b*. These chamfer edges again allow the user to easily guide internal connector 202 positioned on remote manipulator 100 into alignment with adjustable pressure clamp 200 in a manner that allows the user to thereafter extend the manipulator shaft, achieve and maintain alignment between the components, and maintain a secure connection for the purpose of positioning and placing the specific adjustable pressure clamp component during surgery. Removal of the remote manipulator from the adjustable pressure clamp once again involves the retraction of manipulator shaft 105 and the angled separation of the two components as with the previous embodiment shown in FIGS. 8A-8D.

Reference is finally made to FIGS. 10-13A & 13B for a detailed description of a further alternate embodiment of the surgical tool of the present invention wherein the adjustable pressure clamp component is permanently incorporated into the remote manipulator component to form a single surgical tool. This further alternate embodiment is intended to be used primarily by a surgical assistant actively engaged with the surgeon in the securement and placement of tissue and/or organs within the surgical site. This further alternate embodiment of the present invention will find best use as a secondary tool used to either temporarily secure tissue and/or organs or to move such tissue and/or organs within the surgical site rather than to fix a clamp and release it as in the above described preferred embodiments.

Figure 10:
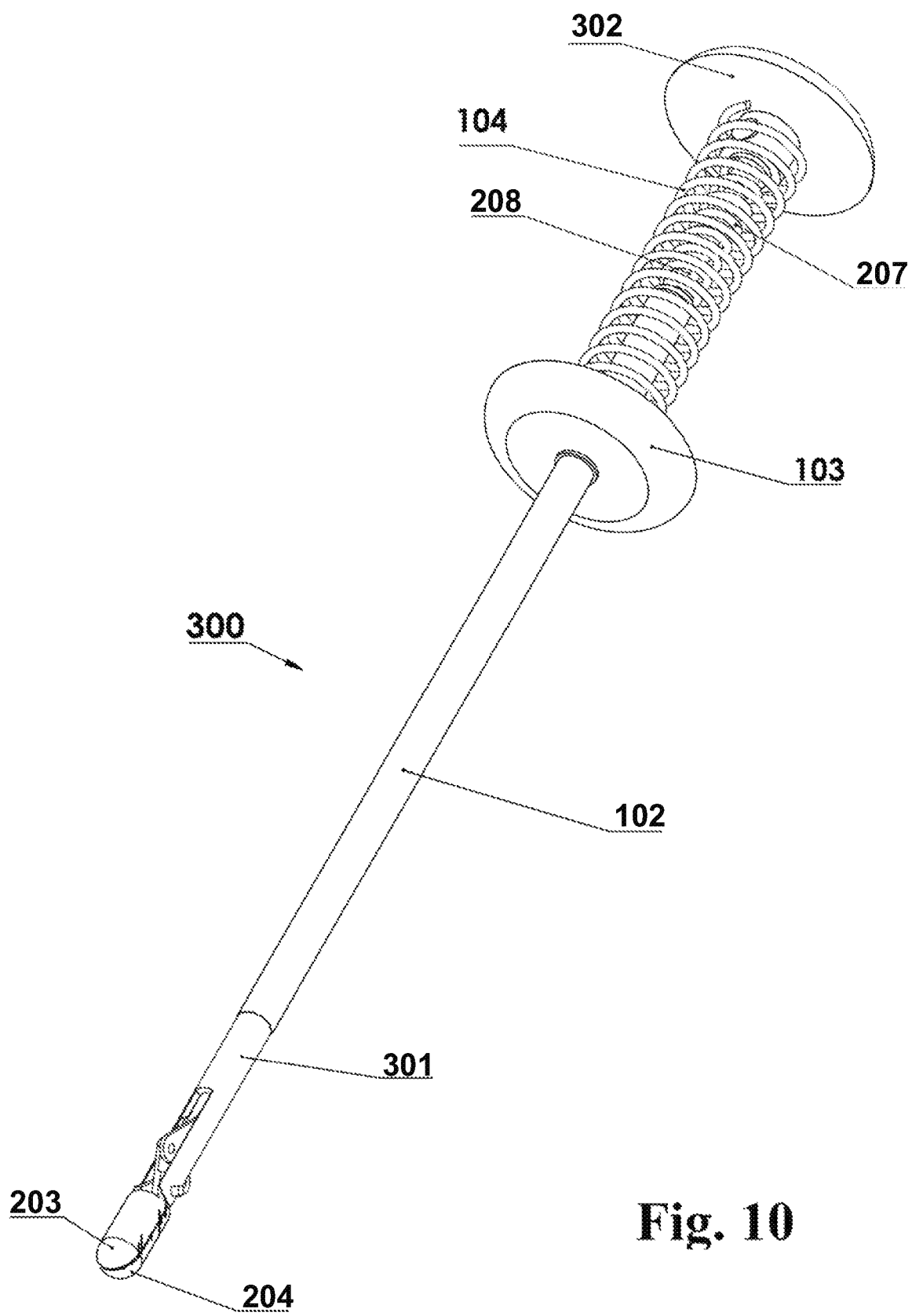
FIG. 10 is a perspective view of a further alternate embodiment of the surgical tool of the present invention with the adjustable pressure clamp component shown in a closed jaw condition and integrated into the remote manipulator component.

FIG. 10 is a perspective view of this further alternate embodiment of the surgical tool of the present invention wherein the adjustable pressure clamp portion of the tool is shown in a closed jaw condition, fully integrated into the remote manipulator portion of the surgical tool. Similar in many respects to the surgical tool shown and described above in FIG. 1, remote manipulated clamp 300 is primarily a rigid outer casing 102 that transitions into clamp body 301 at a distal end and rear manipulator button 302 at a proximal end. Forward manipulator button 103 in this embodiment is again fixed to outer casing 102. Internal to outer casing 102 and extending from the proximal end of the casing is pressure bar 208. In this embodiment outer casing 102 extends proximally beyond forward manipulator button 103 in contrast to the earlier embodiments. This outer casing extension and the proximal end of pressure bar 208 are shown in FIG. 10 surrounded by spring 104. Fixed to the proximal end of pressure bar 208 is rear manipulator button 302 which also serves to contain spring 104 between itself and forward manipulator button 103. With this embodiment however an additional grip adjustment spring 207 is positioned around pressure bar 208 and is fixed between rear manipulator button 302 and the proximal end of outer casing 102. The tension on grip adjustment spring 207 may be adjusted by rotation of rear manipulator button 302 in a manner that compresses or relaxes grip adjustment spring 207 between the manipulator button and the proximal end of outer casing 102. The manner of this adjustment is described in more detail below.

Operation of the remote manipulated clamp 300 as shown in FIG. 10 is generally the same as with the prior embodiments. The user may compress spring 104 and at the same time compress grip adjustment spring 207, using forward and rear manipulator buttons 103 and 302, thereby directing pressure bar 208 into and through outer casing 102. The distal end of remote manipulated clamp 300 shown in FIG. 10 is formed by clamp body 301 which is essentially a threaded extension of outer casing 102 surrounding a single longer pressure bar 208 that extends to directly connect to and operate the jaw assembly of the clamp. First jaw 203 and second jaw 204 are connected to the distal end of pressure bar 208 in the same manner as the pressure bar connected to this jaw assembly in the previously described embodiments. In this further alternate embodiment there is no mechanism for disconnecting clamp body 301 from the balance of remote manipulated clamp 300 as the clamp component here is generally intended for use only with the temporary securement and movement of tissue and/or organs within the surgical site.

Figure 11:
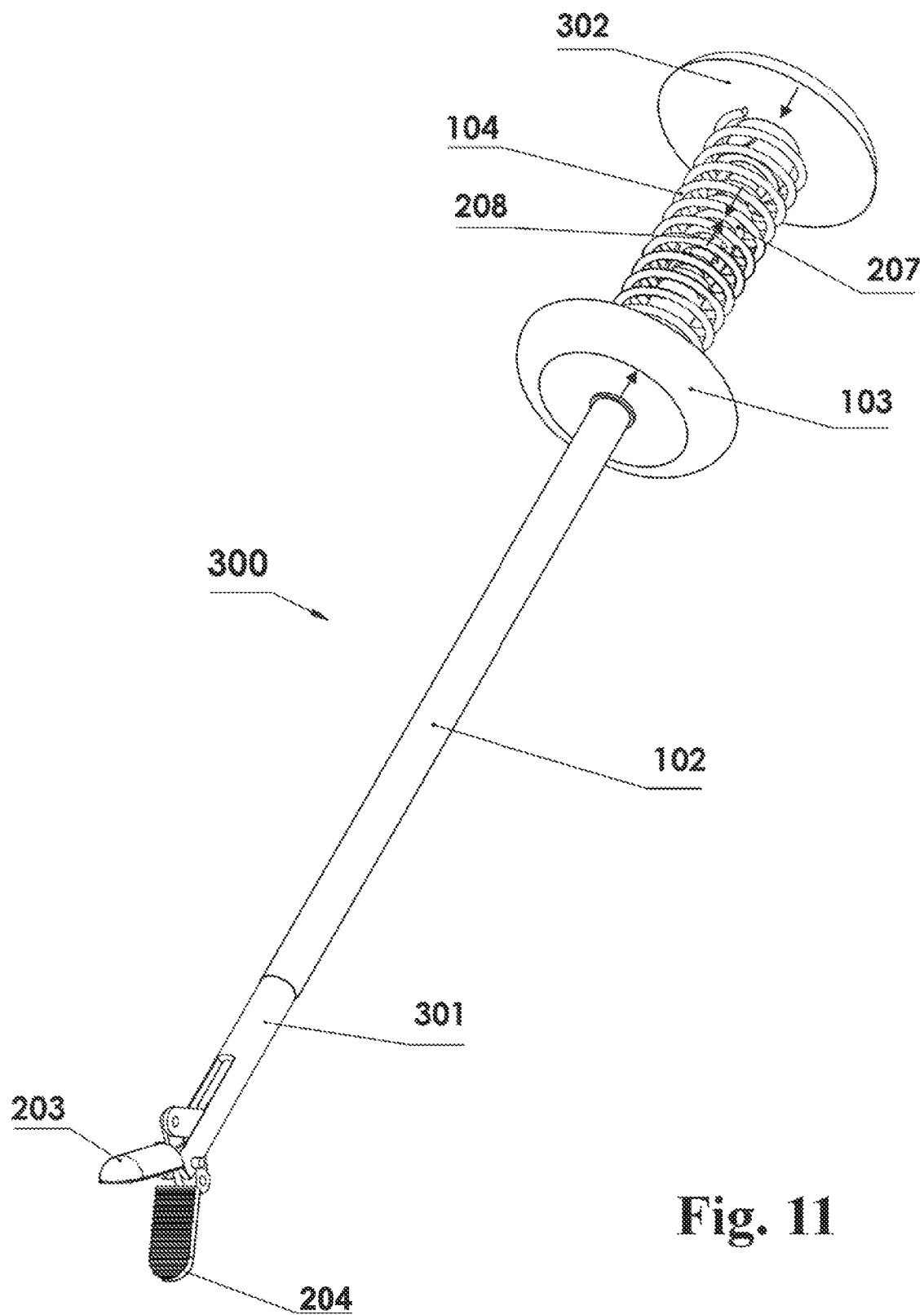
FIG. 11 is a perspective view of the further alternate embodiment of the surgical tool of the present invention as disclosed in FIG. 10, the adjustable pressure clamp component shown in an open jaw condition, integrated into and as directed open by compression of the remote manipulator component.

In the view of FIG. 11, the user has compressed spring 104 (along with grip adjustment spring 207) between forward manipulator button 103 and rear manipulator button 302, thereby directing pressure bar 208 through outer casing 102 of remote manipulated clamp 300. This action directs the distal end of pressure bar 208 through outer casing 102 to its connection with the jaw assembly as described above. This movement thereby opens the jaw assembly with the separation of first jaw 203 from second jaw 204 in the same manner as in the prior embodiments with the adjustable pressure clamp component described therein.

Figure 12A:
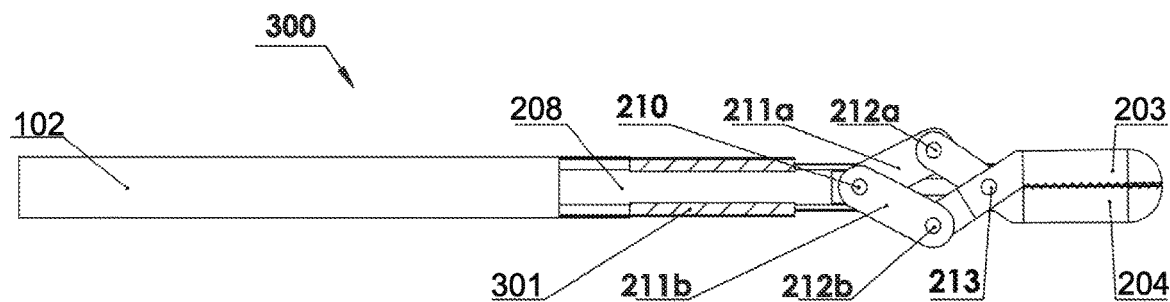
FIG. 12A is a detailed partial cross-sectional view of the further alternate embodiment of the surgical tool of the present invention as disclosed in FIG. 10, the adjustable pressure clamp component shown in a jaw closed condition and integrated into the remote manipulator component.
Figure 12B:
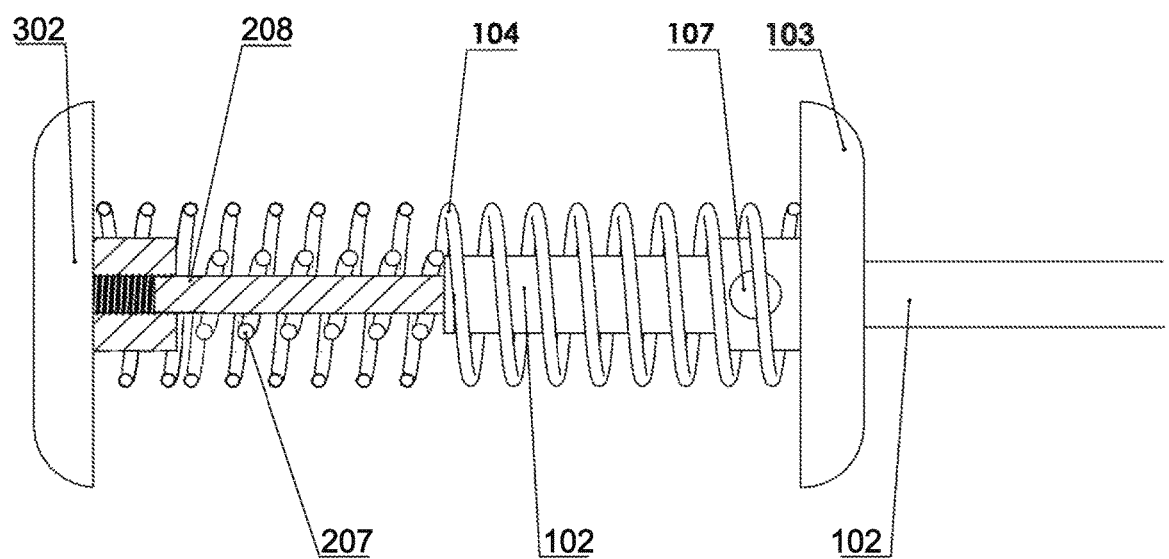
FIG. 12B is a detailed partial cross-sectional view of the handle end of the remote manipulator component of the further alternate embodiment of the surgical tool of the present invention as disclosed in FIG. 10, the remote manipulator component shown in a relaxed (uncompressed) condition, with the internal variable compression spring shown in cross-sectional detail.

FIGS. 12A & 12B are detailed partial cross sectional views of this further alternate embodiment of the surgical tool of the present invention, as disclosed generally in FIG. 10 with the adjustable pressure clamp portion shown in a jaw closed condition, again with the clamp assembly fully integrated into the remote manipulator portion of the surgical tool. More importantly, FIG. 12B shows in greater detail the manner in which adjustment of the clamping force may be carried out using the handle portion of the remote manipulated clamp.

FIG. 12A is a partial cross sectional view that shows the internal structure of the distal end of remote manipulated clamp 300 and the operation of the adjustable pressure clamp assembly at the distal end. The operative gripping end of remote manipulated clamp 300 shown in FIG. 12A includes the distal end of outer casing 102 which is threaded to clamp body 301. Pressure bar 208 extends uninterrupted through outer casing 102 and clamp body 301 to its point of connection at cap screw 210 to cam arms 211a & 211b. As in the previous embodiments, cam arms 211a & 211b connect by way of cam bolts 212a & 212b to first jaw 203 and second jaw 204. This jaw assembly pivots first jaw 203 and second jaw 204 on jaw bolt 213 in a scissor like rotation to direct the closure or the release of the clamp jaws. As in the previous embodiments, jaw bolt 213 is fixed between two parallel yoke plates that extend from clamp body 301.

Reference is next made to FIG. 12B for a detailed description of the manner in which the handle portion of remote manipulated clamp 300 serves to provide the adjustment mechanism to vary the gripping force on the jaw assembly positioned at the opposite end of the tool. As described above, outer casing 102 extends through forward manipulator button 103 which is fixed in this intermediate position on the outer casing using set screw 107. In contrast to the previous embodiments, outer casing 102 extends beyond forward manipulator button 103 in a proximal direction and generally terminates at a midpoint in the gap between forward manipulator button 103 and rear manipulator button 302. This gap again defines the space within which spring 104 is positioned, fixed at a first end to forward manipulator button 103 and at a second end at rear manipulator button 302. Spring 104 therefore provides the return force that expands the gap between the manipulator buttons when the user releases the operative compressive force.

In this further alternate embodiment of the present invention, however, pressure bar 208 is preferenced proximally out from outer casing 102, not only by spring 104 but also by grip adjustment spring 207. Spring 104 provides the minimal necessary force to close the jaws of the clamp assembly, as in the previous embodiments, and also provides a safety mechanism to protect the user's hand or fingers from being pinched by spring 207. More importantly, grip adjustment spring 207 provides an additional force that sets the tightness of the clamp. Grip adjustment spring 207 is positioned and held around pressure bar 208 between the proximal end of outer casing 102 and the collar portion of rear manipulator button 302. Rather than being rigidly fixed to pressure bar 208 in this embodiment, rear manipulator button 302 contains internal threads that engage the external threads on the proximal end of pressure bar 208. This threaded connection allows the user to adjust the gripping force provided by grip adjustment spring 207 by increasing or decreasing the gap between the collar portion of rear manipulator button 302 and the proximal end of outer casing 102. By rotating manipulator button 302 the user may tighten or release the compression in grip adjustment spring 207 thereby increasing or decreasing the force with which pressure bar 208 is pulled proximally out from outer casing 102 and thereby alter the force with which the clamp assembly is held closed. While the clamp assembly may be generally directed into a closed condition by the tension force in spring 104, the force with which the clamp assembly is held closed is primarily determined by the compression that has been preset in grip adjustment spring 207.

Figure 13A:
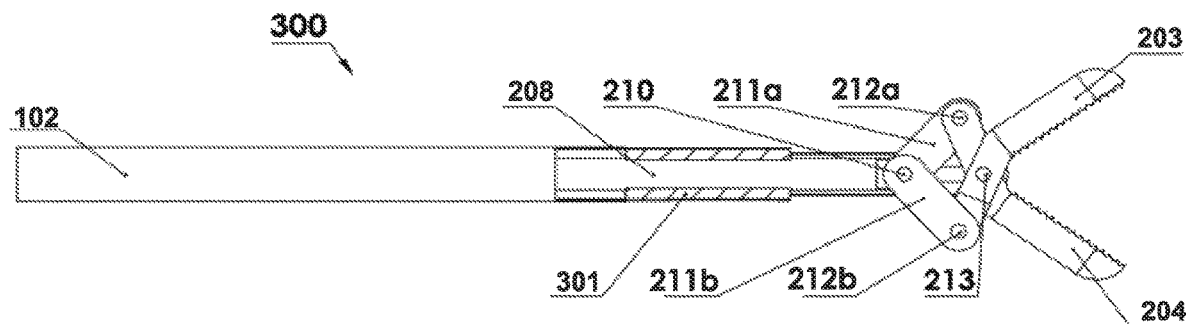
FIG. 13A is a detailed partial cross-sectional view of the further alternate embodiment of the surgical tool of the present invention as disclosed in FIG. 10, the adjustable pressure clamp component shown in a jaw open condition and integrated into the remote manipulator component.
Figure 13B:
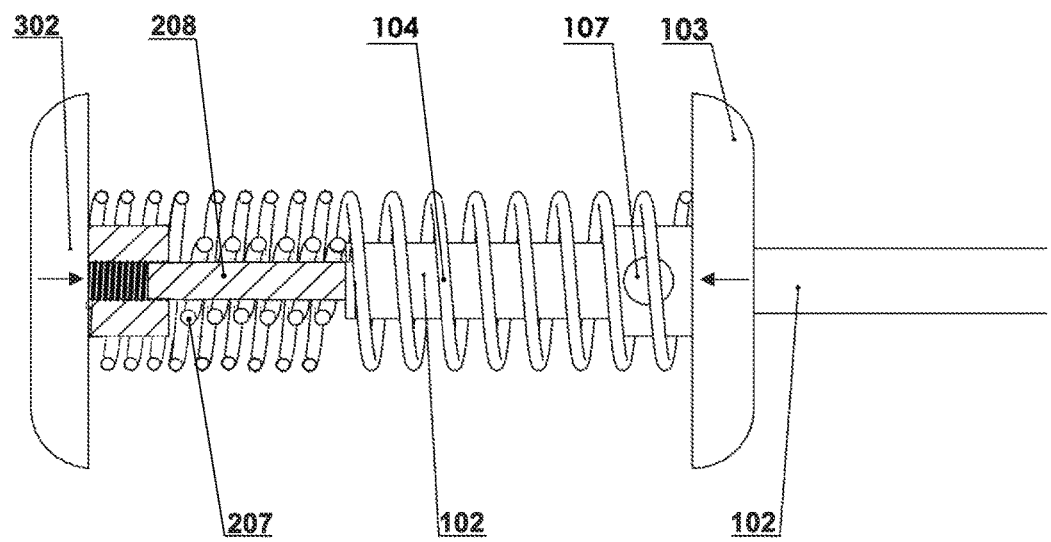
FIG. 13B is a detailed partial cross-sectional view of the handle end of the remote manipulator component of the further alternate embodiment of the surgical tool of the present invention as disclosed in FIG. 10, the remote manipulator component shown in a compressed condition, thereby directing an open jaw condition of the adjustable pressure clamp component as shown in FIG. 13A.

Reference is finally made to FIGS. 13A & 13B for a brief description of the operative structures of the further alternate embodiment of the surgical tool with the remote manipulated clamp 300 shown configured in an open jaw condition. In FIG. 13A, pressure bar 208 is shown to have been directed distally out from outer casing 102 of remote manipulated clamp 300 and through clamp body 301 to direct the jaw assembly distally outward, thereby opening first jaw 203 and second jaw 204 to release the grip of the clamp. This operation is achieved in the manner described above wherein the distal end of pressure bar 208 is secured to cam arms 211a & 211b at cap screw 210 all of which are longitudinally movable with respect to clamp body 301. First jaw 203 and second jaw 204, which are fixed between the yoke plate extensions of clamp body 301 at jaw bolt 213, open by way of a scissor type motion directed by cam arms 211a & 211b acting pivotally on cam bolts 212a & 212b secured to the jaw components.

FIG. 13B shows the process of operating the handle portion of remote manipulated clamp 300 to direct the opening of the jaw assembly as shown in FIG. 13A. The user in this case compresses rear manipulator button 302 together with forward manipulator button 103 in a manner shown by the directional arrows on the manipulator buttons in the figure. This action not only counteracts the force of and compresses spring 104 but also counteracts the force of and compresses grip adjustment spring 207. Pressure bar 208 is directed into outer casing 102 as a result of the user overcoming the expansive forces provided by each of the two spring components.

The two spring components add their expansive forces together to provide the overall clamping force between the jaws of the clamp assembly. While spring 104 provides a fixed expansion force, grip adjustment spring 207, because it may be adjustably compressed in the manner described above, provides an additional clamping force between the jaws. It should be noted that while the user of this further alternate embodiment (typically a surgical assistant) may adjust the clamping force prior to insertion of the tool into the surgical site, the clamping force may also be adjusted while the tool end (the clamping jaws) are positioned within the surgical site. The tool may be initially secured to tissue and/or organs therein and thereafter may be tightened or loosened to vary the clamping force in order to accommodate the optimal grip on the tissue or organ for the specific surgical application or process.

The purpose of this further alternate embodiment of the present invention shown in FIGS. 10-13A & 13B is to provide a clamp that operates to assist with the primary use of the initial embodiments of the present invention that incorporate releasable adjustable clamps. Although primarily serving this function as an assisting tool, this further alternate embodiment may of course operate to carry out other singular steps in the typical laparoscopic or endoscopic surgical procedure.

Although the present invention has been described in connection with a number of different preferred embodiments, those skilled in the art will recognize further embodiments that still fall within the spirit and scope of the invention. Variations in the overall diameter and overall length of the instrument are anticipated. A wide variety of different removable clamp components are anticipated with jaw structures that vary from flat smooth surfaces to serrated surfaces and to specifically configured circular or oval shapes that optimally grip and secure different types of tissue and organs without unnecessary trauma. The devices of the present invention may be constructed of a number of different materials although in the preferred embodiments the components are constructed of stainless steel or other non-corrosive metal materials of the type most surgical tools subject to sterilization are presently constructed.

Each of the first two preferred embodiments of the present invention will potentially benefit from establishing one or both of the adjustable pressure clamp component and the remote manipulator component with magnetic materials or magnetic properties. While making the mechanical connection between the two primary components of the surgical tool is required to open the clamp for attachment to tissue or the like, a much weaker connection as may be established magnetically that allows for the positioning and placement of the releasable clamp component such as for reorientation of the clamp or for clearing the way for additional clamps to be positioned and placed. The use of suture thread (secured through the above described suture apertures on the clamp body) may also be facilitated with the use of magnetically attractive components.

Variations in the specific components and arrangements of the jaw assembly are also anticipated. As an example, one jaw element may be fixed on the clamp body with the second opposing jaw element subject to the manipulator motion of the tool. Other variations in the structure and geometry of the preferred embodiments of the present invention are anticipated. The primary objectives of the present invention are satisfied by the ability of the surgeon to quickly and accurately position and place multiple clamp elements within a confined surgical site to carry out the many and varied steps associated with typical laparoscopic and endoscopic procedures.

We claim:

1. A remotely manipulable variable pressure clamp for use in laparoscopic and endoscopic surgeries, the clamp having a proximal handle portion and a distal gripping portion, the clamp comprising:
   (a) a longitudinal tubular casing extending from the proximal handle portion to the distal gripping portion;
   (b) a pressure bar slidingly positioned within and extending the length of the tubular casing;
   (c) a first finger grip button flange fixed to the tubular casing at a point distally offset from a proximal end of the tubular casing;
   (d) a second finger grip button flange fixed to a proximal end of the pressure bar;
   (e) an adjustable compression assembly positioned and operable within the handle portion of the clamp, the adjustable compression assembly comprising:
      (i) an operative spring positioned coaxially around the tubular casing and the pressure bar and between the first and second finger grip button flanges, the operative spring preferencing the button flanges apart, thereby preferencing the pressure bar to extend proximally from the tubular casing; and
      (ii) a clamp compression spring positioned coaxially around a proximal end of the pressure bar and between the second finger grip button flange and a proximal end face of the tubular casing; and
   (f) a clamp body forming the distal gripping portion of the clamp, the clamp body comprising a movable jaw assembly.

2. The variable pressure clamp of claim 1 wherein the adjustable compression assembly preferences the movable jaw assembly into a normally closed condition and the extension of the pressure bar operatively into the clamp body directs the movable jaw assembly into an open condition.

3. The variable pressure clamp of claim 1 wherein the adjustable compression assembly further comprises a threaded portion on the proximal end of the pressure bar and a threaded portion of the second finger grip button flange, the second finger grip button flange threadingly engaging the proximal end of the pressure bar, wherein rotation of the second finger grip button flange moves the flange along the length of the threaded proximal end of the pressure bar and thereby increases or decreases the space between the second finger grip button flange and the proximal end face of the tubular casing, thereby increasing or decreasing the tension in the clamp compression spring positioned there between.

* * * * *